(12) United States Patent
Van Der Linden et al.

(10) Patent No.: US 7,863,501 B2
(45) Date of Patent: Jan. 4, 2011

(54) B-TYPE GENE FROM OIL PALM

(75) Inventors: Cornelis Gerardus Van Der Linden, Bennekom (NL); Sharifah Shahrul Rabiah Syed Alwee, Selangor (MY); Marinus Johannes Maria Smulders, Ka Ugchelen (NL); Cheah Suan Choo, Selangor (MY); Meilina Ong Bt. Abdullah, Selangor (MY); Ooi Siew Eng, Selangor (MY)

(73) Assignee: Malaysian Palm Oil Board, Selangor (MY)

( * ) Notice: Subject to any disclaimer, the term of this patent is extended or adjusted under 35 U.S.C. 154(b) by 345 days.

(21) Appl. No.: 11/243,296

(22) Filed: Sep. 30, 2005

(65) Prior Publication Data

US 2006/0112449 A1 May 25, 2006

(30) Foreign Application Priority Data

Sep. 30, 2004 (MY) .............................. PI 20044004

(51) Int. Cl.
- *C12N 15/29* (2006.01)
- *C12N 15/82* (2006.01)
- *C12N 15/87* (2006.01)
- *C12N 5/04* (2006.01)

(52) U.S. Cl. ..................... 800/278; 536/23.1; 536/23.6; 435/320.1; 435/410; 435/419

(58) Field of Classification Search ........................ None
See application file for complete search history.

(56) References Cited

PUBLICATIONS

Alwee et al (2006, Plant Cell, Tissue and Organ Culture 85:331-344).*
Kang et al (1995, Plant Molecular Biology 29(1):1-10).*
Bowie et al, Science 247:1306-1310, 1990.*
McConnell et al, Nature 411 (6838):709-713, 2001.*
Oommenn et al (1994, The Plant Cell 6:1789-1803).*
Spangenberg et al (2002, DERWENT Accession No. ABK82089).*
Nakamura et al (2003, NCBI Accession No. AB079259).*
Song et al (2004, NCBI Accession No. AY621156).*

* cited by examiner

*Primary Examiner*—Stuart F. Baum
(74) *Attorney, Agent, or Firm*—Knobbe Martens Olson & Bear LLP

(57) ABSTRACT

The present invention relates generally to genetic sequences and their complementary forms capable of facilitating the modification of a phenotype of a plant. More particularly, the present invention relates to polynucleotide sequences defining B-type genes, to the proteins encoded thereby, to methods for isolating such polynucleotides and to nucleic acid constructs for the expression thereof. The present invention further provides cells, particularly transformed bacterial or plant cells and to differentiated tissue including whole plants and their progeny comprising cells which contain these nucleic acid constructs or parts of the constructs. Plants and parts of plants, such as flowering and reproductive parts including seeds, also form part of the present invention. The genetic sequences of the present invention may be used inter alia for the production of plants and, in particular, oil palm plants, which have modified phenotypes and/or which exhibits more highly desired characteristics such as, for example, male sterility or plants in which the sex ratio may be manipulated, and for the diagnosis and, preferably, elimination of the mantled phenotype.

27 Claims, 7 Drawing Sheets

```
GTCTCTCTC TCTTCTTTCG CGATCAAACT CGATTAGTAC GAGTACACAA CCCTCCATTT
CCAGTGGCGG GGTCTGAACC ACCCCGAAAG CCatgtcctc cccttcccca agatggaagc
ctcttccctt ctcctctcct tccctccgcc tttatctttc tccctatctc ttcatcaccg
ccttcatcca tcctttctct cttctccatc tcgatctcct tcttcggtga tctccggcga
gtgcgggcgg cggcggcggg gaccaaaATG GGGCGAGGGA AGATTGAGAT TAAGCGGATC
GAGAACTCCA CCAACCGGCA AGTGACCTTC TCCAAGCGGC GGAATGGGAT CATCAAGAAG
GCACGGGAGA TCAGCGTCCT CTGCGATGCC CAGGTCTCCG TCGTCATCTT CTCCAGCTCC
GGCAAGATGT CCGAGTACTG CAGCCCCTCC ACCACGCTGT CGAGGATTCT CGAGAGGTAC
CAGCATAACT CTGGCAAGAA GCTCTGGGAT GCCAAGCACG AGAGTCTTAG TGCTGAGATC
GACCGGATCA AGAAAGAGAA TGACAACATG CAGATCGAGC TGAGGCATTT GAAGGGTGAG
GATCTGAACT CACTGAGCCC AAAGGAACTC ATTCCAATTG AAGATGCCCT CCAGAATGGT
CTCATCAGTG TTCGGGACAA GCAGATGGAG TTCTTGAAGA AGCTCAAGAA GAATGAGAGA
TTGCTGGAAG AGGAGAACAA GCATCTGACT TATCTATTGC ACCAGCAGGA ATTGGCAATG
GATGCAAATG TAAGGGAACT GGAGCTTGGA TATCCTTCGA AAGATAGGGA TTTTGCTTCC
CACATGCCAC TAGCCTTCCA TGTGCAACCA ATCCAGCCTA ATTTGCAAGA GAACAATTAA
tataaaagtt ctccttatgt ttagttggtc ttctcttttg gtgttaaatt gtctgtagac
atgtactgtt tttcaactct tgtattttc tatactctca ctatttccc tgtctgaatc
agcaaaagaa ctcatttga tgtgctaata gatgcctggt ttagctg
```

FIGURE 1

```
            10         20         30         40         50         60
     caacccgaaa gtatagatcc caaacaatct cattcataat gtttagtgtt ccttctttgt
            70         80         90        100        110        120
     gttttctttc atgtgagaag atactcaatt cttgcacttt cctttatttc gtatggtccg
           130        140        150        160        170        180
     gtagctccat ttacttccct tggagcttaa atacaaagta tgccaaaaga gtAcataatt
           190        200        210        220        230        240
     ttaaatacca atataatcca ttattttccc caatttgaaa ttgctgtagt aataaattta
           250        260        270        280        290        300
     ctttcttgca cacgcatcgt cgagaatcca tcagtgtaat cagtttcata aataacacgt
           310        320        330        340        350        360
     gaagcagtcc aaaacaatat aatagaaaat aaacatcaat tagaagataa atattacaat
           370        380        390        400        410        420
     ctcttttata tttttaacat tataggca aatattgatt aaagaaaaaa atcacaggtg
           430        440        450        460        470        480
     agtaaaatgt catagcaaaa gtgaacactt tcattctata tattatctac acgtagtttt
           490        500        510        520        530        540
     tatttataat atttaattaa atattaatta tttatttaat ttatcatatt tatcgtaaga
           550        560        570        580        590        600
     tttatcacca ctatcaatga tatgaatgtc gaaattttta aacagcagca taaattgtct
           610        620        630        640        650        660
     tagaatattc gaaacgatat atagtagttg aagtttatc cattttttta agaatattcg
           670        680        690        700        710        720
     gatctgcctt cgtaatttca ttgtaatttc tgtttagcac atctttagaa agatgaatag
           730        740        750        760        770        780
     tattattggt tgaatcgtct tctatatttt tttaataaaa taaaatattt ttataaaata
           790        800        810        820        830        840
     aatatcaata taatttaaaa aattaaaaaa aatatcataa aaaatttcaa taaattacat
           850        860        870        880        890        900
     acatcagacc aaacatccgt tccaaacatg attaacaaca tagttagcaa ttcattcgat
           910        920        930        940        950        960
     ggtactattt atctctcagt gcatatattt cacattgata agcatacaat atgtaataac
           970        980        990       1000       1010       1020
     atgccagatg tcatgtatgg gcggattgga ggccgagctc tcgtatataa ctgggatgtg
          1030       1040       1050       1060       1070       1080
     tgatcacatc tgacatgcgg attagttccg tcctaaatct tataggatgt tttattttt
          1090       1100       1110       1120       1130       1140
     ttgatctttt gagatgtact tgtgtgagca tccgtctgta tcaattaaaa aaaacaaaaa
          1150       1160       1170       1180       1190       1200
     aaaaaaaaca gcggcataag cgaacacgtt ctctttcgtc cgtctctctc tcttctttcg
          1210       1220       1230       1240       1250       1260
     cgatcaaact cgattagtac gagtacacaa ccctccattt ccagtggcgg ggtctgaacc
          1270       1280       1290       1300       1310       1320
     accccgaaag ccatgtcctc cccttcccca agatggaagc ctcttccctt ctcctctcct
          1330       1340       1350       1360       1370       1380
     tccctccgcc tttatctttc tccctatctc ttcatcaccg ccttcatcca tcctttctct
          1390       1400       1410       1420       1430       1440
     cttctccatc tcgatctcct tcttcggtga tctccggcga gtgcgggcgg cggcggcggg
          1450       1460       1470       1480       1490       1500
     gaccaaaATG GGGCGAGGGA AGATTGAGAT TAAGCGGATC GAGAACTCCA CCAACCGGCA
          1510       1520       1530       1540       1550       1560
     AGTGACCTTC TCCAAGCGGC GGAATGGGAT CATCAAGAAG GCACGGGAGA TCAGCGTCCT
          1570       1580       1590       1600       1610       1620
```

FIGURE 2A

```
CTGCGATGCC CAGGTCTCCG TCGTCATCTT CTCCAGCTCC GGCAAGATGT CCGAGTACTG
    1630       1640       1650       1660       1670       1680
CAGCCCCTCC ACCACgtatt actctgcccc cttctatctc tctcggtgtc tttctctttc
    1690       1700       1710       1720       1730       1740
tctgtgtttc ttttaaccat tttgtcatta tatttgatgg gattgaagGC TGTCGAGGAT
    1750       1760       1770       1780       1790       1800
TCTCGAGAGG TACCAGCATA ACTCTGGCAA GAAGCTCTGG GATGCCAAGC ACGAGgtagg
    1810       1820       1830       1840       1850       1860
tctcggattt aaccctattg cttgctgttt tttgttcaga aaaaaatcgt tttttttatga
    1870       1880       1890       1900       1910       1920
atggaagtga tgagaaaaga gagattttgc aacttggtag cgaatctatg aatacgcgtt
    1930       1940       1950       1960       1970       1980
gggaagaacc tgagccaaat gtttcagttt catgtattgc tgaaacgaaa cgataagaaa
    1990       2000       2010       2020       2030       2040
atggatattt gaaagaaga acctagttga tggatggaag tgataaaaag gagaaatttt
    2050       2060       2070       2080       2090       2100
gcaactggct tacgaacttc tggaaatcct tatcagaatc tttattctct ttcctctctt
    2110       2120       2130       2140       2150       2160
cctcttgcgt tgttgtaaat tcatgtttag atggaaagaa gggataaaga agagaagttt
    2170       2180       2190       2200       2210       2220
agctatttgt tgattaattt ctgggaacct gttacagAGT CTTAGTGCTG AGATCGACCG
    2230       2240       2250       2260       2270       2280
GATCAAGAAA GAGAATGACA ACATGCAGAT CGAGCTGAGG CATTTGAAGG GTGAGGATCT
    2290       2300       2310       2320       2330       2340
GAACTCACTG AGCCCAAAGG AACTCATTCC AATTGAAGAT GCCCTCCAGA ATGGTCTCAT
    2350       2360       2370       2380       2390       2400
CAGTGTTCGG GACAAGCAGA TGGAGTTCTT GAAGAAGCTC AAGAAGAATG AGAGATTGCT
    2410       2420       2430       2440       2450       2460
GGAAGAGGAG AACAAGCATC TGACTTATCT ATTGCACCAG CAGGAATTGG CAATGGATGC
    2470       2480       2490       2500       2510       2520
AAATGTAAGG GAACTGGAGC TTGGATATCC TTCGAAAGAT AGGGATTTTG CTTCCCACAT
    2530       2540       2550       2560       2570       2580
GCCACTAGCC TTCCATGTGC AACCAATCCA GCCTAATTTG CAAGAGAACA ATTAAataa
    2590       2600       2610       2620       2630       2640
aagttctcct tatgtttagt tggtcttctc ttttggtgtt aaattgtctg tagacatgta
    2650       2660       2670       2680       2690       2700
ctgtttttca actcttgtat ttttctatac tctcactatt ttccctgtct gaatcagcaa
    2710       2720       2730       2740
aagaactcat ttggatgtgc taatagatgc ctggtttagc tg
```

[ATG]    Start codon

A      mutation at nucleotide "-1274"

Capital letters: open reading frame

Bold: exon

Plain: intron

[TAA]    stop codon

FIGURE 2B

Fig. 3: RT-PCR with specific primers for EgMADS genes.
Lanes1/2: Shoot apex normal/abnormal
Lanes 3-10: Inflorescences :
2.5cm/6cm/10cm female normal (3/4/5), 13cm male normal (6), 2.5cm/6cm/10cm female abnormal (7/8/9), 28cm male normal (10)
Lane 11: water control A
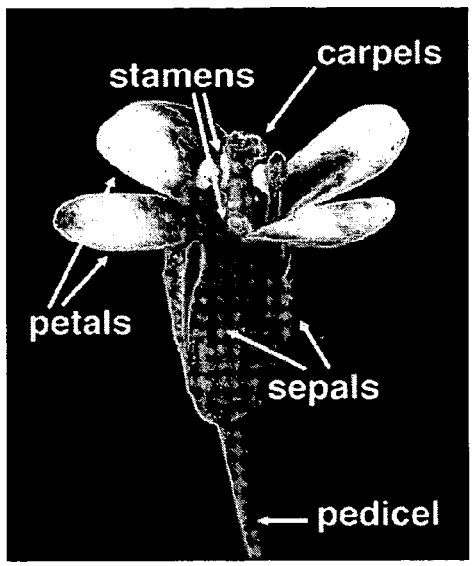
B
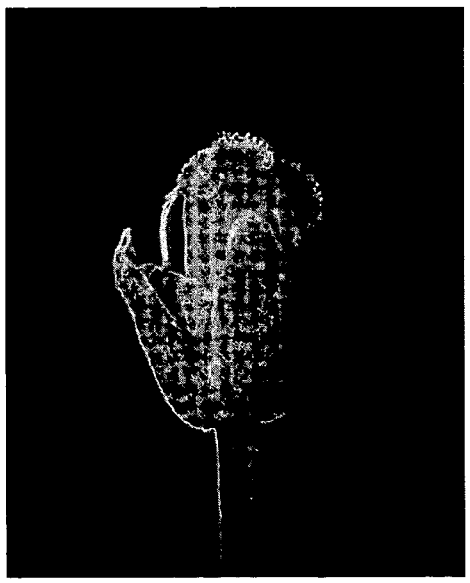
C
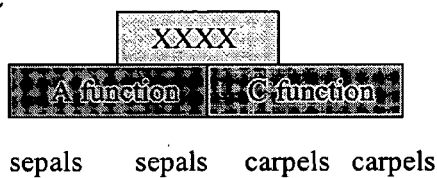
sepals    sepals    carpels    carpels
FIGURE 4

SEQUENCE LISTING

<160> NUMBER OF SEQ ID NOS: 27

<210> SEQ ID NO 1
<211> LENGTH: 633
<212> TYPE: DNA
<213> ORGANISM: Elaeis guineensis
<220> FEATURE:

<221> NAME/KEY: CDS
<222> LOCATION: (1)..(633)

<400> SEQUENCE: 1

```
atg ggg cga ggg aag att gag att aag cgg atc gag aac tcc acc aac      48
Met Gly Arg Gly Lys Ile Glu Ile Lys Arg Ile Glu Asn Ser Thr Asn
1               5                   10                  15 cgg caa gtg acc ttc tcc aag cgg cgg aat ggg atc atc aag aag gca      96
Arg Gln Val Thr Phe Ser Lys Arg Arg Asn Gly Ile Ile Lys Lys Ala
                20                  25                  30 cgg gag atc agc gtc ctc tgc gat gcc cag gtc tcc gtc gtc atc ttc     144
Arg Glu Ile Ser Val Leu Cys Asp Ala Gln Val Ser Val Val Ile Phe
            35                  40                  45 tcc agc tcc ggc aag atg tcc gag tac tgc agc ccc tcc acc acg ctg     192
Ser Ser Ser Gly Lys Met Ser Glu Tyr Cys Ser Pro Ser Thr Thr Leu
        50                  55                  60 tcg agg att ctc gag agg tac cag cat aac tct ggc aag aag ctc tgg     240
Ser Arg Ile Leu Glu Arg Tyr Gln His Asn Ser Gly Lys Lys Leu Trp
65                  70                  75                  80 gat gcc aag cac gag agt ctt agt gct gag atc gac cgg atc aag aaa     288
Asp Ala Lys His Glu Ser Leu Ser Ala Glu Ile Asp Arg Ile Lys Lys
                85                  90                  95 gag aat gac aac atg cag atc gag ctg agg cat ttg aag ggt gag gat     336
Glu Asn Asp Asn Met Gln Ile Glu Leu Arg His Leu Lys Gly Glu Asp
                100                 105                 110 ctg aac tca ctg agc cca aag gaa ctc att cca att gaa gat gcc ctc     384
Leu Asn Ser Leu Ser Pro Lys Glu Leu Ile Pro Ile Glu Asp Ala Leu
            115                 120                 125 cag aat ggt ctc atc agt gtt cgg gac aag cag atg gag ttc ttg aag     432
Gln Asn Gly Leu Ile Ser Val Arg Asp Lys Gln Met Glu Phe Leu Lys
        130                 135                 140 aag ctc aag aag aat gag aga ttg ctg gaa gag gag aac aag cat ctg     480
Lys Leu Lys Lys Asn Glu Arg Leu Leu Glu Glu Glu Asn Lys His Leu
145                 150                 155                 160 act tat cta ttg cac cag cag gaa ttg gca atg gat gca aat gta agg     528
Thr Tyr Leu Leu His Gln Gln Glu Leu Ala Met Asp Ala Asn Val Arg
                165                 170                 175 gaa ctg gag ctt gga tat cct tcg aaa gat agg gat ttt gct tcc cac     576
Glu Leu Glu Leu Gly Tyr Pro Ser Lys Asp Arg Asp Phe Ala Ser His
                180                 185                 190 atg cca cta gcc ttc cat gtg caa cca atc cag cct aat ttg caa gag     624
Met Pro Leu Ala Phe His Val Gln Pro Ile Gln Pro Asn Leu Gln Glu
            195                 200                 205 aac aat taa                                                          633
Asn Asn
    210
```

<210> SEQ ID NO 2
<211> LENGTH: 210
<212> TYPE: PRT
<213> ORGANISM: Elaeis guineensis

<400> SEQUENCE: 2

```
Met Gly Arg Gly Lys Ile Glu Ile Lys Arg Ile Glu Asn Ser Thr Asn
1               5                   10                  15

Arg Gln Val Thr Phe Ser Lys Arg Arg Asn Gly Ile Ile Lys Lys Ala
                20                  25                  30

Arg Glu Ile Ser Val Leu Cys Asp Ala Gln Val Ser Val Val Ile Phe
            35                  40                  45

Ser Ser Ser Gly Lys Met Ser Glu Tyr Cys Ser Pro Ser Thr Thr Leu
```

```
            50                  55                  60
Ser Arg Ile Leu Glu Arg Tyr Gln His Asn Ser Gly Lys Lys Leu Trp
 65                  70                  75                  80

Asp Ala Lys His Glu Ser Leu Ser Ala Glu Ile Asp Arg Ile Lys Lys
                 85                  90                  95

Glu Asn Asp Asn Met Gln Ile Glu Leu Arg His Leu Lys Gly Glu Asp
            100                 105                 110

Leu Asn Ser Leu Ser Pro Lys Glu Leu Ile Pro Ile Glu Asp Ala Leu
            115                 120                 125

Gln Asn Gly Leu Ile Ser Val Arg Asp Lys Gln Met Glu Phe Leu Lys
130                 135                 140

Lys Leu Lys Lys Asn Glu Arg Leu Leu Glu Glu Asn Lys His Leu
145                 150                 155                 160

Thr Tyr Leu Leu His Gln Gln Glu Leu Ala Met Asp Ala Asn Val Arg
                165                 170                 175

Glu Leu Glu Leu Gly Tyr Pro Ser Lys Asp Arg Asp Phe Ala Ser His
            180                 185                 190

Met Pro Leu Ala Phe His Val Gln Pro Ile Gln Pro Asn Leu Gln Glu
        195                 200                 205

Asn Asn
    210

<210> SEQ ID NO 3
<211> LENGTH: 1066
<212> TYPE: DNA
<213> ORGANISM: Elaeis guineensis

<400> SEQUENCE: 3
gtctctctct cttcttcgc gatcaaactc gattagtacg agtacacaac cctccatttc      60
cagtggcggg gtctgaacca ccccgaaagc catgtcctcc ccttcccaa gatggaagcc     120 tcttcccttc tcctctcctt ccctccgcct ttatctttct ccctatctct tcatcaccgc     180
cttcatccat cctttctctc ttctccatct cgatctcctt cttcggtgat ctccggcgag     240
tgcgggcggc ggcggcgggg accaaaatgg ggcgagggaa gattgagatt aagcggatcg     300
agaactccac caaccggcaa gtgaccttct ccaagcggcg gaatgggatc atcaagaagg     360
cacgggagat cagcgtcctc tgcgatgccc aggtctccgt cgtcatcttc tccagctccg     420
gcaagatgtc cgagtactgc agcccctcca ccacgctgtc gaggattctc gagaggtacc     480
agcataactc tggcaagaag ctctgggatg ccaagcacga gagtcttagt gctgagatcg     540
accggatcaa gaaagagaat gacaacatgc agatcgagct gaggcatttg aagggtgagg     600
atctgaactc actgagccca aaggaactca ttccaattga agatgccctc cagaatggtc     660
tcatcagtgt tcgggacaag cagatggagt tcttgaagaa gctcaagaag aatgagagat     720
tgctggaaga ggagaacaag catctgactt atctattgca ccagcaggaa ttggcaatgg     780
atgcaaatgt aagggaactg gagcttggat atccttgcaa agataaggat tttgcttccc     840
acatgccact agccttccat gtgcaaccaa tccagcctaa tttgcaagag aacaattaat     900
ataaaagttc tccttatgtt tagttggtct tctcttttgg tgttaaattg tctgtagaca     960
tgtactgttt ttcaactctt gtattttct atactctcac tattttccct gtctgaatca    1020
gcaaaagaac tcatttggat gtgctaatag atgcctggtt tagctg                 1066

<210> SEQ ID NO 4
<211> LENGTH: 1447
```

<212> TYPE: DNA
<213> ORGANISM: Elaeis guineensis

<400> SEQUENCE: 4

```
caacccgaaa gtatagatcc caaacaatct cattcataat gtttagtgtt ccttctttgt      60
gttttctttc atgtgagaag atactcaatt cttgcacttt cctttatttc gtatggtccg     120
gtagctccat ttacttccct tggagcttaa atacaaagta tgccaaaaga gtacataatt     180
ttaaatacca atataatcca ttattttccc caatttgaaa ttgctgtagt aataaattta     240
ctttcttgca cacgcatcgt cgagaatcca tcagtgtaat cagtttcata ataacacgt      300
gaagcagtcc aaaacaatat aatagaaaat aaacatcaat tagaagataa atattacaat     360
ctcttttata tttttaacat tatataggca aatattgatt aaagaaaaaa atcacaggtg     420
agtaaaatgt catagcaaaa gtgaacactt tcattctata tattatctac acgtagtttt     480
tatttataat atttaattaa atattaatta tttatttaat ttatcatatt tatcgtaaga     540
tttatcacca ctatcaatga tatgaatgtc gaaattttta aacagcagca taaattgtct     600
tagaatattc gaaacgatat atagtagttg aagtttatc cattttttta agaatattcg      660
gatctgcctt cgtaatttca ttgtaatttc tgtttagcac atctttagaa agatgaatag     720
tattattggt tgaatcgtct tctatatttt tttaataaaa taaatatttt ttataaaata     780
aatatcaata taatttaaaa aattaaaaaa aatatcataa aaaatttcaa taaattacat     840
acatcagacc aaacatccgt tccaaacatg attaacaaca tagttagcaa ttcattcgat     900
ggtactattt atctctcagt gcatatattt cacattgata agcatacaat atgtaataac     960
atgccagatg tcatgtatgg gcggattgga ggccgagctc tcgtatataa ctgggatgtg    1020
tgatcacatc tgacatgcgg attagttccg tcctaaatct tataggatgt tttatttttt    1080
ttgatctttt gagatgtact tgtgtgagca tccgtctgta tcaattaaaa aaaacaaaaa    1140
aaaaaaaaca gcggcataag cgaacacgtt ctctttcgtc cgtctctctc tcttctttcg    1200
cgatcaaact cgattagtac gagtacacaa ccctccattt ccagtggcgg ggtctgaacc    1260
accccgaaag ccatgtcctc cccttcccca agatggaagc ctcttccctt ctcctctcct    1320
tccctccgcc tttatctttc tccctatctc ttcatcaccg ccttcatcca tcctttctct    1380
cttctccatc tcgatctcct tcttcggtga tctccggcga gtgcgggcgg cggcggcggg    1440
gaccaaa                                                             1447
```

<210> SEQ ID NO 5
<211> LENGTH: 93
<212> TYPE: DNA
<213> ORGANISM: Elaeis guineensis

<400> SEQUENCE: 5

```
gtattactct gccccttct atctctctcg gtgtctttct ctttctctgt gtttctttta      60
accattttgt cattatattt gatgggattg aag                                  93
```

<210> SEQ ID NO 6
<211> LENGTH: 402
<212> TYPE: DNA
<213> ORGANISM: Elaeis guineensis

<400> SEQUENCE: 6

```
gtaggtctcg gatttaaccc tattgcttgc tgttttttgt tcagaaaaaa atcgttttt      60
tatgaatgga agtgatgaga aaagagagat tttgcaactt ggtagcgaat ctatgaatac    120
```

-continued

```
gcgttgggaa gaacctgagc caaatgtttc agtttcatgt attgctgaaa cgaaacgata    180
agaaaatgga tatttgaaaa gaagaaccta gttgatggat ggaagtgata aaaggagaa     240 attttgcaac tggcttacga acttctggaa atccttatca gaatctttat tctctttcct    300
ctcttcctct tgcgttgttg taaattcatg tttagatgga agaagggat aaagaagaga     360 agtttagcta tttgttgatt aatttctggg aacctgttac ag                      402
```

<210> SEQ ID NO 7
<211> LENGTH: 20
<212> TYPE: DNA
<213> ORGANISM: Artificial Sequence
<220> FEATURE:
<223> OTHER INFORMATION: MADS3' primer

<400> SEQUENCE: 7
acctcrgcrt crcaaragsac                                               20

<210> SEQ ID NO 8
<211> LENGTH: 20
<212> TYPE: DNA
<213> ORGANISM: Artificial Sequence
<220> FEATURE:
<223> OTHER INFORMATION: MADS5' primer

<400> SEQUENCE: 8
agytsaagmg gatmgagaac                                                20

<210> SEQ ID NO 9
<211> LENGTH: 21
<212> TYPE: DNA
<213> ORGANISM: Artificial Sequence
<220> FEATURE:
<223> OTHER INFORMATION: MADS5'B primer

<400> SEQUENCE: 9
aagatmaara gratmgagaa c                                              21

<210> SEQ ID NO 10
<211> LENGTH: 21
<212> TYPE: DNA
<213> ORGANISM: Artificial Sequence
<220> FEATURE:
<223> OTHER INFORMATION: KBOX-DOWN primer

<400> SEQUENCE: 10
atrttrtcrt tstctttctt g                                              21

<210> SEQ ID NO 11
<211> LENGTH: 21
<212> TYPE: DNA
<213> ORGANISM: Artificial Sequence
<220> FEATURE:
<223> OTHER INFORMATION: MADS17 primer

<400> SEQUENCE: 11
accckgaagg tgawcggcat c                                              21

<210> SEQ ID NO 12
<211> LENGTH: 25
<212> TYPE: DNA
<213> ORGANISM: Artificial Sequence
<220> FEATURE:
<223> OTHER INFORMATION: MADS3-5 primer
<220> FEATURE:
<221> NAME/KEY: modified_base

```
<222> LOCATION: (9)..(9)
<223> OTHER INFORMATION: n=i
<220> FEATURE:
<221> NAME/KEY: modified_base
<222> LOCATION: (15)..(15)
<223> OTHER INFORMATION: n=i
<220> FEATURE:
<221> NAME/KEY: modified_base
<222> LOCATION: (18)..(18)
<223> OTHER INFORMATION: n=i

<400> SEQUENCE: 12
cgscgyttns mraangtnac ctgsc                                        25

<210> SEQ ID NO 13
<211> LENGTH: 21
<212> TYPE: DNA
<213> ORGANISM: Artificial Sequence
<220> FEATURE:
<223> OTHER INFORMATION: MADS10 primer

<400> SEQUENCE: 13
caagatgtcc gagtactgca g                                           21

<210> SEQ ID NO 14
<211> LENGTH: 21
<212> TYPE: DNA
<213> ORGANISM: Artificial Sequence
<220> FEATURE:
<223> OTHER INFORMATION: MADS11 primer

<400> SEQUENCE: 14
ctgcagtact cggacatctt g                                           21

<210> SEQ ID NO 15
<211> LENGTH: 21
<212> TYPE: DNA
<213> ORGANISM: Artificial Sequence
<220> FEATURE:
<223> OTHER INFORMATION: MADS12 primer

<400> SEQUENCE: 15
gctgtcgagg attctcgaga g                                           21

<210> SEQ ID NO 16
<211> LENGTH: 21
<212> TYPE: DNA
<213> ORGANISM: Artificial Sequence
<220> FEATURE:
<223> OTHER INFORMATION: MADS13 primer

<400> SEQUENCE: 16
ctctcgagaa tcctcgacag c                                           21

<210> SEQ ID NO 17
<211> LENGTH: 21
<212> TYPE: DNA
<213> ORGANISM: Artificial Sequence
<220> FEATURE:
<223> OTHER INFORMATION: MADS14 primer

<400> SEQUENCE: 17
gaggtaccag cataactctg g                                           21

<210> SEQ ID NO 18
<211> LENGTH: 21
<212> TYPE: DNA
```

<213> ORGANISM: Artificial Sequence
<220> FEATURE:
<223> OTHER INFORMATION: MADS15 primer

<400> SEQUENCE: 18
ccagagttat gctggtacct c                                              21

<210> SEQ ID NO 19
<211> LENGTH: 23
<212> TYPE: DNA
<213> ORGANISM: Artificial Sequence
<220> FEATURE:
<223> OTHER INFORMATION: MADS18 primer

<400> SEQUENCE: 19
gagaagatac tcaattcttg cac                                            23

<210> SEQ ID NO 20
<211> LENGTH: 21
<212> TYPE: DNA
<213> ORGANISM: Artificial Sequence
<220> FEATURE:
<223> OTHER INFORMATION: MADS19 primer

<400> SEQUENCE: 20
tgtgtactcg tactaatcga g                                              21

<210> SEQ ID NO 21
<211> LENGTH: 21
<212> TYPE: DNA
<213> ORGANISM: Artificial Sequence
<220> FEATURE:
<223> OTHER INFORMATION: MADS20 primer

<400> SEQUENCE: 21
aggtgagtaa aatgtcatag c                                              21

<210> SEQ ID NO 22
<211> LENGTH: 32
<212> TYPE: DNA
<213> ORGANISM: Artificial Sequence
<220> FEATURE:
<223> OTHER INFORMATION: Linker-long oligonucleotide

<400> SEQUENCE: 22
actcgattct caacccgaaa gtatagatcc ca                                  32

<210> SEQ ID NO 23
<211> LENGTH: 18
<212> TYPE: DNA
<213> ORGANISM: Artificial Sequence
<220> FEATURE:
<223> OTHER INFORMATION: Linker-short oligonucleotide

<400> SEQUENCE: 23
tgggatctat actttcaa                                                  18

<210> SEQ ID NO 24
<211> LENGTH: 14
<212> TYPE: DNA
<213> ORGANISM: Artificial Sequence
<220> FEATURE:
<223> OTHER INFORMATION: Linker-short-NH2 oligonucleotide

<400> SEQUENCE: 24
tgggatctat actt                                                      14

```
<210> SEQ ID NO 25
<211> LENGTH: 21
<212> TYPE: DNA
<213> ORGANISM: Artificial Sequence
<220> FEATURE:
<223> OTHER INFORMATION: ADAPT-Pr oligonucleotide

<400> SEQUENCE: 25
actcgattct caacccgaaa g                                              21

<210> SEQ ID NO 26
<211> LENGTH: 22
<212> TYPE: DNA
<213> ORGANISM: Artificial Sequence
<220> FEATURE:
<223> OTHER INFORMATION: ADAPT-Pr2 oligonucleotide

<400> SEQUENCE: 26
caacccgaaa gtatagatcc ca                                             22

<210> SEQ ID NO 27
<211> LENGTH: 2742
<212> TYPE: DNA
<213> ORGANISM: Elaeis guineensis

<400> SEQUENCE: 27
caacccgaaa gtatagatcc caaacaatct cattcataat gtttagtgtt ccttctttgt      60
gttttctttc atgtgagaag atactcaatt cttgcacttt cctttatttc gtatggtccg     120
gtagctccat ttacttccct tggagcttaa atacaaagta tgccaaaaga gtacataatt     180
ttaaatacca atataatcca ttattttccc caatttgaaa ttgctgtagt aataaattta     240
ctttcttgca cacgcatcgt cgagaatcca tcagtgtaat cagtttcata ataacacgt      300 gaagcagtcc aaaacaatat aatagaaaat aaacatcaat tagaagataa atattacaat     360
ctcttttata tttttaacat tatataggca aatattgatt aaagaaaaaa atcacaggtg     420
agtaaaatgt catagcaaaa gtgaacactt tcattctata tattatctac acgtagtttt     480
tatttataat atttaattaa atattaatta tttatttaat ttatcatatt tatcgtaaga     540
tttatcacca ctatcaatga tatgaatgtc gaaatttta aacagcagca taaattgtct      600
tagaatattc gaaacgatat atagtagttg aagttttatc cattttttta agaatattcg     660
gatctgcctt cgtaatttca ttgtaatttc tgtttagcac atctttagaa agatgaatag     720
tattattggt tgaatcgtct tctatatttt tttaataaaa taaaatattt ttataaaata     780
aatatcaata taatttaaaa aattaaaaaa aatatcataa aaaatttcaa taaattacat     840
acatcagacc aaacatccgt tccaaacatg attaacaaca tagttagcaa ttcattcgat     900
ggtactattt atctctcagt gcatatattt cacattgata agcatacaat atgtaataac     960
atgccagatg tcatgtatgg gcggattgga ggccgagctc tcgtatataa ctgggatgtg    1020
tgatcacatc tgcatgcgg attagttccg tcctaaatct tataggatgt ttattttt      1080 ttgatctttt gagatgtact tgtgtgagca tccgtctgta tcaattaaaa aaaacaaaaa    1140
aaaaaaaaca gcggcataag cgaacacgtt ctctttcgtc cgtctctctc tcttctttcg    1200
cgatcaaact cgattagtac gagtacacaa ccctccattt ccagtggcgg ggtctgaacc    1260
accccgaaag ccatgtcctc cccttcccca agatggaagc ctcttccctt ctcctctcct    1320
tccctccgcc tttatctttc tcctatctc ttcatcaccg ccttcatcca tcctttctct    1380
```

```
                                                      -continued
cttctccatc tcgatctcct tcttcggtga tctccggcga gtgcgggcgg cggcggcggg    1440
gaccaaaatg gggcgaggga agattgagat taagcggatc gagaactcca ccaaccggca    1500
agtgaccttc tccaagcggc ggaatgggat catcaagaag gcacgggaga tcagcgtcct    1560
ctgcgatgcc caggtctccg tcgtcatctt ctccagctcc ggcaagatgt ccgagtactg    1620
cagcccctcc accacgtatt actctgcccc cttctatctc tctcggtgtc tttctctttc    1680
tctgtgtttc ttttaaccat tttgtcatta tatttgatgg gattgaaggc tgtcgaggat    1740
tctcgagagg taccagcata actctggcaa gaagctctgg gatgccaagc acgaggtagg    1800
tctcggattt aaccctattg cttgctgttt tttgttcaga aaaaaatcgt tttttttatga   1860 atggaagtga tgagaaaaga gagattttgc aacttggtag cgaatctatg aatacgcgtt    1920
gggaagaacc tgagccaaat gtttcagttt catgtattgc tgaaacgaaa cgataagaaa    1980
atggatattt gaaaagaaga acctagttga tggatggaag tgataaaaag gagaaatttt    2040
gcaactggct tacgaacttc tggaaatcct tatcagaatc tttattctct ttcctctctt    2100
cctcttgcgt tgttgtaaat tcatgtttag atggaaagaa gggataaaga agagaagttt    2160
agctatttgt tgattaattt ctgggaacct gttacagagt cttagtgctg agatcgaccg    2220
gatcaagaaa gagaatgaca acatgcagat cgagctgagg catttgaagg gtgaggatct    2280
gaactcactg agcccaaagg aactcattcc aattgaagat gccctccaga atggtctcat    2340
cagtgttcgg gacaagcaga tggagttctt gaagaagctc aagaagaatg agagattgct    2400
ggaagaggag aacaagcatc tgacttatct attgcaccag caggaattgg caatggatgc    2460
aaatgtaagg gaactggagc ttggatatcc ttcgaaagat agggattttg cttcccacat    2520
gccactagcc ttccatgtgc aaccaatcca gcctaatttg caagagaaca attaatataa    2580
aagttctcct tatgtttagt tggtcttctc ttttggtgtt aaattgtctg tagacatgta    2640
ctgtttttca actcttgtat ttttctatac tctcactatt ttccctgtct gaatcagcaa    2700
aagaactcat ttggatgtgc taatagatgc ctggtttagc tg                      2742
```

B-TYPE GENE FROM OIL PALM

BACKGROUND OF THE INVENTION

1. Field of the Invention

The present invention relates generally to genetic sequences and their complementary forms capable of facilitating the modification of a phenotype of a plant. More particularly, the present invention relates to polynucleotide sequences defining B-type MADS box genes, to the proteins encoded thereby, to methods for isolating such polynucleotides and to nucleic acid constructs for the expression thereof. The present invention further provides cells, particularly transformed bacterial or plant cells and to differentiated tissue including whole plants and their progeny comprising cells which contain these nucleic acid constructs or parts of the constructs. Plants and parts of plants, such as flowering and reproductive parts including seeds, also form part of the present invention. The genetic sequences of the present invention may be used inter alia for the production of plants and, in particular, oil palm plants, which have modified phenotypes and/or which exhibit more highly desired characteristics such as, for example, male sterility or plants in which the sex ratio may be manipulated, and for the diagnosis and, preferably, elimination of the mantled phenotype.

2. Description of the Related Art

Reference to any prior art in this specification is not, and should not be taken as, an acknowledgment or any form of suggestion that this prior art forms part of the common general knowledge in any country.

The architecture of flowers is determined by the activity of a number of homeotic genes, typically containing a conserved MADS box domain. The MADS box is a highly conserved sequence domain found in a family of transcription factors. Most MADS domain factors play a key role in developmental processes. In particular, the MADS box genes of flowering plants are the molecular architects of flower architecture.

In both *Arabidopsis thaliana* and *Antirrhinum majus*, two B-type genes have been identified. These genes—also known as organ identity genes—specify petal and stamen development. In *Arabidopsis*, APETALA3 (AP3) and PISTILLATA (PI) are B-type genes. Mutations in either gene disrupt the specification of petal and stamen identity, thereby converting the petals in the second whorls to sepals, and stamens in the third whorl into carpels. Both genes are part of a large family of MADS-box genes that play a central role in the development of flowers. In *Antirrhinum*, DEFICIENS (DEF) and GLOBOSA (GLO) are B-type genes and together they also control development of petals and stamens. Mutant analysis and binding studies suggest that, in these species, the B-type genes are functional as a heterodimer in specifying the B-function. Consequently, changes in expression in any of the two genes may affect the B-type activity, and hence the organ identity of the second and/or third whorl.

The MADS box gene concept appears to apply to a wide range of plant species, including monocotyledons and trees, with minor adjustments. Notably, in some species more than two B-type genes have been tentatively identified. In Norway spruce, for example, DAL11, DAL12 and DAL13 are related to B-type genes. However, in this plant, it was found that the B-type genes function as both organ identity genes and meristem identity genes, indicating that they have evolved differently in conifers and angiosperms. Recent results suggest that for proper B-type function, expression of additional MADS box genes from the AGL-like gene family is required (Egea-Cortinez et al., *EMBO J.* 18: 5370-5379, 1999; Honma and Goto, *Nature* 409: 525-529, 2001). These MADS box genes code for proteins that interact with the B-type heterodimer complex, forming a ternary complex. This third partner may be essential for transcriptional activation of genes coding for downstream processes.

Monocotyledonous plant species that frequently suffer from the adverse effects of inappropriate and/or incorrect flower development, are the oil palm trees of the species *Elaeis guineensis* and *Elaeis oleifera*. Trees of these species, which produce palm oil and palm kernel oil, comprise the highest yielding oil crop in the world. The demand for oil and fats is expected to increase dramatically with the increase in world population. Oil palm plantations were forecast to contribute around a quarter of the world's oil and fats demand by the year 2020 (Rajanaidu and Jalani, In Proceedings of 1995 Palm Oil Research Institute of Malaysia—National Oil Palm Conference.—Technologies in Plantation, The Way Forward, pp. 1-29, 1995).

Of particular concern, therefore, is the fact that mutant plants, exhibiting a so-called "mantled" phenotype, are frequently produced during what are becoming routine procedures used for plantation development and replenishment; namely, micropropagation of oil palm plantlets via somatic embryogenesis and/or organogenesis. Since their inception, micropropagation techniques have been found to produce phenotypic variability through somaclonal variation. In clonal progeny from oil palm plants, approximately 5% have been found to exhibit the abnormal "mantled" flower phenotype. This phenotype is characterized by the feminisation of the third whorl in the flowers of both sexes. Such mantled plants develop abnormally and are frequently sterile, thereby directly affecting oil production. The cause of the mantled phenotype is unknown, and studies of ploidy level and polymorphism have not shown relevant genomic changes.

Due to the increased demand for plantation oil palm and palm oil, there is a concomitant need to increase the quality and yield of palm oil and palm kernel oil. An understanding of the phenomenon that leads to mantling is, therefore, critical. There is also a need to develop diagnostic protocols for mantling and to be able to prevent it from occurring altogether. Furthermore, there is an associated need to be able to rapidly develop new plant/oil characteristics when required.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided at the end of the specification.

The present invention provides genetic molecules encoding B-type MADS box-type transcription factors which are involved in flower differentiation and development. The genetic molecules may comprise genomic sequences optionally including the promoter region, genomic sequences comprising exons and introns, cDNA molecules comprising linked exon sequences, protein sequences thereby determined and individual or contiguous intron and exon sequences. All of such genetic sequences and proteins have application in the generation of transgenic plants displaying useful characteristics.

The plants may be monocotyledonous or dicotyledonous plants although monocotyledonous plants are preferred. Particularly preferred plants are oil palm plants of the genus *Elaeis*. Even more preferred species are, for example, *Elaeis guineensis* and *Elaeis oleifera*.

Accordingly, one aspect of the present invention provides an isolated nucleic acid molecule comprising a sequence of nucleotides encoding or complementary to a sequence encoding a polypeptide comprising the amino acid sequence set forth in SEQ ID NO:2 or an amino acid sequence having at least about 70% similarity thereto, generally after optimal alignment.

Another aspect of the present invention provides an isolated nucleic acid molecule comprising a nucleotide sequence set forth in SEQ ID NO:1 or SEQ ID NO:3 or a nucleotide sequence having at least about 70% identity thereto after optimal alignment or a nucleotide sequence capable of hybridizing to SEQ ID NO:1 or SEQ ID NO:3 or its complementary form under low stringency conditions at 42° C.

The nucleic acid molecules of the present invention may be used in the preparation of chimeric genetic constructs that comprise in addition or inter alia one or more regulatory regions such as promoters and 5' upstream enhancer regions and 3' sequences. In an alternative embodiment, a nucleotide sequence defining the genomic region beginning from either the "ATG" start codon or the putative transcription initiation start site, and including the 3' sequence, may be inserted into the construct. In any case, genetic constructs so constituted may then serve as vectors for the transformation of target plant material in order to deliver the means for adding or subtracting a desirable trait or phenotype.

Accordingly, another aspect of the present invention is directed to a genetic construct comprising a nucleotide sequence selected from SEQ ID NO:1 or one or more of SEQ ID NO:3 to SEQ ID NO:6 inclusive or a nucleotide sequence having at least 70% similarity to one or more of SEQ ID NO:1 or SEQ ID NO:3 to SEQ ID NO:6 inclusive or a nucleotide sequence capable of hybridizing to SEQ ID NO:1 or SEQ ID NO:3 to SEQ ID NO:6 inclusive or a complementary form of these sequences under low stringency conditions at 42° C.

Once a chimeric genetic construct has been cloned into a vector and introduced into target plant material, the exogenously introduced coding sequence may be expressed by the cell to cause the production of the encoded protein, in this case a transcription factor. The action of the introduced protein may effect a desirable phenotype that would otherwise not be present.

In a related embodiment, the present invention therefore provides a vector for use in generating transgenic plants exhibiting modified phenotypes, said transgenic plants producing a polypeptide comprising an amino acid sequence as set forth in SEQ ID NO:2 or an amino acid sequence having at least 70% similarity to SEQ ID NO:2.

The polypeptide having the amino acid sequence set forth in SEQ ID NO:2 is an example of a MADS-box comprising protein which is referred to herein as a MADS-like protein, The present invention extends to any protein comprising a MADS box domain, whether the protein is naturally occurring or artificially created, wherein the protein comprises an amino acid sequence having at least 70% similarity to SEQ ID NO:2 and encodes a transcription factor which, in its naturally occurring state, is involved in determining flower differentiation and development.

An example of an artificially created protein is a fusion or chimeric protein comprising a portion from at least one protein comprising a MADS-box domain and a portion of another protein.

Hence, another aspect of the invention provides an isolated polypeptide, or a biologically active fragment thereof, said polypeptide comprising an amino acid sequence set forth in SEQ ID NO:2 or an amino acid sequence having at least 70% similarity to the sequence set forth in SEQ ID NO: 2.

The present invention further contemplates promoter regions that may also include associated 5' regulatory regions, which provide a mechanism whereby the control of expression of an introduced nucleic acid molecule may be effected. It may be necessary and/or desirable to direct the expression of the exogenously introduced sequence to the appropriate tissue, for example, or to cause its expression in a developmentally regulated manner. Alternatively, constitutive expression may be desirable. The contemplated promoter region of the present invention is the natural promoter of the isolated nucleic acid molecule set forth in SEQ ID NO:3 which, in vivo, is operably linked to the nucleic acid molecule.

Accordingly, in a related aspect, the present invention provides an isolated polynucleotide defining a promoter region and comprising a sequence of nucleotides as set forth in SEQ ID NO:4, or a sequence having at least about 70% identity thereto or a nucleotide sequence capable of hybridizing to SEQ ID NO:4 or its complementary form under low stringency conditions at 42° C.

The polynucleotide promoter region of the present invention may be utilized, as described above, in the generation of a genetic construct, which comprises the polynucleotide promoter operably linked to a nucleic acid molecule of the present invention and appropriate 3' sequences. The 3' sequences may be those also derived from the same isolated and cloned genetic sequences set forth herein or, alternatively, may be derived from other heterologous sequences. Furthermore, the polynucleotide promoter may be utilized in the generation of a chimeric genetic construct, which comprises the promoter together with other heterologous nucleic acid molecules. Hence, the isolated polynucleotide promoter may be used to drive the expression of any genetic sequence capable of being used to provide and/or withdraw a particular phenotype to or from a target cell into which it is introduced.

Therefore, the nucleic acid sequences disclosed herein may be applied to alter or modulate a particular trait/phenotype of a target cell or tissue in a plant. This may be effected, for example, by providing the cDNA encoding the transcription factor, or by providing a genomic clone thereof complete with its associated intron sequences, in either case driven by its own or a heterologous promoter region. Alternatively, modulation may be effected by providing a chimeric genetic construct comprising the polynucleotide promoter of the present invention driving another heterologous nucleic acid sequence.

Accordingly, still another aspect of the present invention contemplates a method for generating a plant with a modified phenotype, said method comprising introducing into the genome of a plant cell or group of plant cells a genetic construct comprising a polynucleotide promoter region or functional equivalent thereof operably linked to a nucleotide sequence encoding a MADS-like polypeptide having an amino acid sequence as set forth in SEQ ID NO:2 or an amino acid sequence having at least 70% similarity to the sequence set forth in SEQ ID NO:2.

A MADS-like polypeptide includes a MADS polypeptide.

The promoter region may be the polynucleotide of the present invention or it may be any other suitable promoter, of which there are numerous known in the art.

In yet another alternative embodiment, the modified trait or phenotype may be effected via modulation of the expression of an endogenous gene, using an introduced genetic construct comprising, for example, selected genomic intron and/or exon sequences. This aspect of the present invention is based on the proposal that intron and exon sequences are involved in genetic networking. The introns or exons may act as receiver sequences or signal sequences.

Yet another aspect of the present invention therefore contemplates an intron defined by an isolated genomic sequence comprising a sequence of nucleotides as set forth in SEQ ID NO:5 or SEQ ID NO:6 or a sequence having at least about 70% identity thereto or a sequence capable of hybridizing to SEQ ID NO:5 or SEQ ID NO:6 or complementary forms thereof under low stringency conditions at 42° C.

A summary of sequence identifiers used throughout the subject specification is provided in Table 1.

TABLE 1

1. Summary of sequence identifiers

| SEQUENCE ID NO. | NAME | DESCRIPTION |
|---|---|---|
| 1 | EgMADS1-CDS | nucleotide sequence of protein-encoding DNA |
| 2 | EgMADS1 protein | translated predicted amino acid sequence |
| 3 | EgMADS1 mRNA | nucleotide sequence of cDNA defining the from mRNA putative transcription initiation start site, including 5' non-translated region, CDS and 3' non-translated region |
| 4 | EgMADS1 5' flanking region | genomic polynucleotide defining the up-stream 5' sequences of the Eg MADS1 gene, including promoter and 5' non-translated sequence |
| 5 | EgMADS1 intron #1 | nucleotide sequence of first intron in the DNA coding region |
| 6 | EgMADS1 intron #2 | nucleotide sequence of second intron in the DNA coding region |
| 7 | MADS3' | consensus nucleotide primer sequence - amplification direction into MADS box from 3' end |
| 8 | MADS5' | consensus nucleotide primer sequence - amplification direction into MADS box from 5' beginning |
| 9 | MADS5'B | consensus nucleotide primer sequence - amplification direction into MADS box, optimized for B-type genes |
| 10 | KBOX-DOWN | consensus nucleotide primer sequence - amplification direction from K-box towards MADS-box, optimized for B-type genes |
| 11 | MADS17 | consensus nucleotide primer sequence - amplification direction from end of coding sequence towards K-box, based on rice B-type genes |
| 12 | MADS3-5 | consensus nucleotide primer sequence - amplification direction in middle of MADS box, based on oil palm MADS boxes |
| 13 | MADS10 | nucleotide primer designed on the EgMADS1 (clone Kbox2a) sequence - towards K-box |
| 14 | MADS11 | nucleotide primer designed on the EgMADS1 (clone Kbox2a) sequence - towards MADS-box |
| 15 | MADS12 | nucleotide primer designed on the EgMADS1 (clone Kbox2a) sequence - towards K-box |
| 16 | MADS13 | nucleotide primer designed on the EgMADS1 (clone Kbox2a) sequence - towards MADS-box |
| 17 | MADS14 | nucleotide primer designed on the EgMADS1 (clone Kbox2a) sequence - towards K-box |
| 18 | MADS15 | nucleotide primer designed on the EgMADS1 (clone Kbox2a) sequence - towards MADS-box |

TABLE 1-continued

1. Summary of sequence identifiers

| SEQUENCE ID NO. | NAME | DESCRIPTION |
|---|---|---|
| 19 | MADS18 | nucleotide primer designed on the Hpa 1.6 kb genomic fragment - towards coding sequence |
| 20 | MADS19 | nucleotide primer designed on the Hpa 1.6 kb genomic fragment - towards promoter sequence |
| 21 | MADS20 | nucleotide primer designed on the Hpa 1.6 kb genomic fragment - towards coding sequence |
| 22 | Linker-long | long nucleotide linker sequence |
| 23 | Linker-short | short nucleotide linker sequence |
| 24 | Linker-short-NH2 | short nucleotide linker sequence |
| 25 | ADAPT-Pr | nucleotide primer sequence |
| 26 | ADAPT-Pr2 | nucleotide primer sequence |
| 27 | MADS21 | nucleotide primer designed on the EgMADS1 (clone Kbox2a) sequence - towards MADS-box |
| 28 | MADS22 | nucleotide primer designed on the EgMADS1 3'- noncoding sequence - towards 5'-end of the gene |

BRIEF DESCRIPTION OF THE DRAWINGS

FIG. 1 is a representation showing the nucleotide sequence of the EgMADS1 cDNA clone (SEQ ID NO: 3). The sequence includes the putative transcription initiation start site and the 5' non-translated region—shown in lower case letters—as well as the 3' regulatory region—also shown in lower case letters. The coding sequence that is translated is shown in upper case letters. "ATG"=start codon; "TAA"=stop codon; "ACCAC"=end of exon 1; "ACGAG"=end of exon 2.

FIGS. 2A (SEQ ID NO: 27) and 2B are representations showing a compilation of sequence information derived from genomic and cDNA clones comprising the following nucleic acid molecules of the present invention: a genomic nucleotide sequence defining part of the EgMADS1 gene; genomic sequence defining the 5' flanking region, including the promoter and 5' non-translated sequence; the CDS of the EgMADS1 protein, the genomic sequence defining 2 introns, and the 3' regulatory region. Lower case letters indicate an untranslated region, while upper case letters indicate exon open reading frame sequence that is translated. One exception is the "G" to "A" mutation at position "−1274", which may be seen as a capital letter in the early part of the lower case promoter region, at the position numbered 173 in the figure. The start codon "ATG" is boxed. The "TAA" stop codon occurs at the end of the open reading frame and is also boxed.

FIG. 4 consists of photographic representations of (A) wild type Arabidopsis flower and (B) a pi mutant, and (C) a diagrammatic representation of the ABC model for the pi mutant, indicating that mutation in the "B-type" sequence causes the development of sepals and carpels only, while petal and stamen development is prevented.

DETAILED DESCRIPTION OF THE PREFERRED EMBODIMENT

Figure 3:
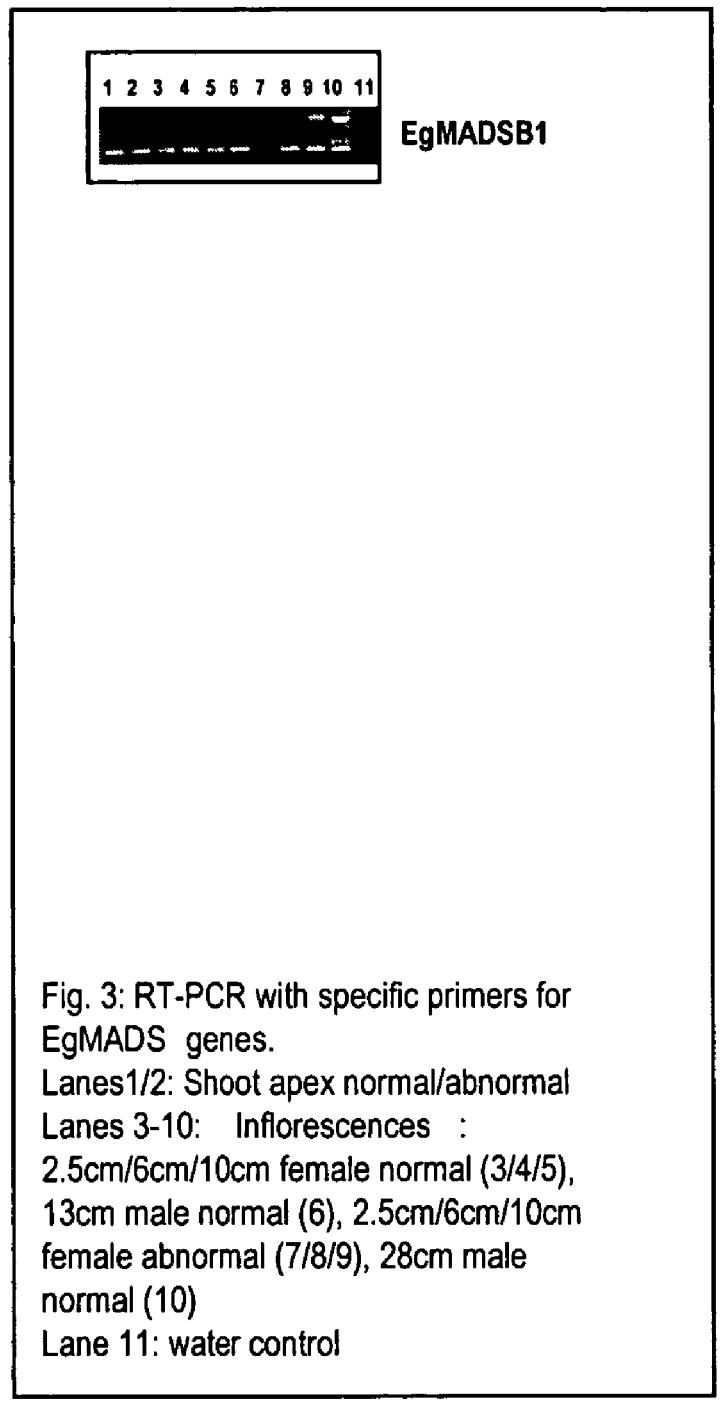
FIG. 3 is a photographic representation of an agarose gel following RT-PCR of oil palm tissue with specific primers for EgMADS genes. Lanes 1 and 2: shoot apex normal and abnormal, respectively. Lanes 3 to 10: inflorescences at 2.5 cm, 6 cm, 10 cm female normal (lanes 3, 4 and 5, respectively); 13 cm male normal (lane 6); 2.5 cm, 6 cm, 10 cm female abnormal (lanes 7, 8 and 9, respectively); 28 cm male normal (lane 10). Lane 11: water control.

The present invention provides genetic molecules which encode B-type MADS-like proteins from plant species *Elaeis guineensis* and *Elaeis oleifera*.

Accordingly, one aspect of the present invention provides an isolated nucleic acid molecule comprising a sequence of nucleotides encoding or complementary to a sequence encoding a B-type MADS-like polypeptide comprising the amino acid sequence set forth in SEQ ID NO:2 or an amino acid sequence having at least about 70% similarity thereto.

In a related embodiment, the present invention provides an isolated nucleic acid molecule comprising a sequence of nucleotides as set forth in SEQ ID NO:1 or SEQ ID NO:3 or a nucleotide sequence having at least about 70% identity thereto after optimal alignment or a nucleotide sequence capable of hybridizing to SEQ ID NO:1 or SEQ ID NO:3 or its complementary form under low stringency conditions at 42° C.

Reference herein to a "nucleic acid molecule" includes reference to DNA, cDNA or RNA (e.g. mRNA and rRNA) as well as DNA/DNA and DNA/RNA hybrids. A nucleic acid molecule may also be referred to herein inter alia as a genetic molecule, nucleotide sequence or polynucleotide sequence. Reference to a DNA molecule includes genomic DNA. In one preferred embodiment, the nucleic acid molecule is a cDNA molecule although the present invention extends to genomic forms of the nucleic acid molecule.

By "isolated" is meant material that is substantially or essentially free from components that normally accompany it in its native state. For example, an "isolated nucleic acid molecule" as used herein refers to a nucleic acid molecule, which has been purified from the sequences which flank it in a naturally-occurring state, e.g. a DNA fragment which has been removed from the sequences which are normally adjacent to the fragment. Preferably but not necessarily, an isolated nucleic acid molecule is in a form capable of being sequenced (i.e. sequencably pure).

The term "nucleic acid molecule" or other terms such as "genetic molecule" of the present invention encompasses derivatives, including mutants and homologs thereto.

By "derivative" is meant any single or multiple nucleotide deletions, additions or substitutions as well as mutants, fragments, portions or parts of the isolated nucleic acid molecule. All such deletions, additions, substitutions, mutants, fragments, portions, or parts are encompassed by the term "derivative". Particularly useful derivatives include alterations to the 5' end portion of the polynucleotide sequence or the 3' end portion or a nucleotide sequence spanning the 5' and 3' portions. Synthetic derivatives may also be useful, for example, in diagnostic assays. A derivative also conveniently includes a nucleotide sequence having less than 100% identity with the nucleotide sequence set forth in SEQ ID NO:1 or SEQ ID NO:3 to SEQ ID NO:6 inclusive but which is capable of hybridizing thereto or their complementary forms under low stringency conditions at 42° C.

Reference herein to a "polypeptide" includes reference to a peptide or protein. The polypeptide of the present invention is produced via expansion of the nucleotide sequences herein disclosed and functions during flower differentiation and development. The processes involved in normal "flower differentiation and development" include the production of flowering parts such as but not limited to the pistils (also called carpels), anthers, ovaries, sepals and petals of the flowering region. Mutation in one of more genes involved in determining flower differentiation and development may lead to malformation of one or more flower parts and concomitant malfunction of the plant in other ways. For example, without wishing to limit the invention to any one theory or mode of action, it is proposed that malformation of flower architecture in plants of the oil palm species *E. guineensis* and *E. oleifera* leads to the "mantled" phenotype. This phenotype is characterised by partial or complete sterility, thereby directly affecting the ability of the oil palm plant to produce oil. The ability to intercede and prevent the development of the mantled phenotype or to diagnose it in early micropropagated plant material provides the oil palm industry with the means to prevent the present economic losses incurred through plant and, hence, oil losses.

One way in which to achieve that is through the use of molecular markers to identify the appropriate genetic locus and to determine the presence or not of a relevant mutation associated with the undesirable phenotype. The availability of the nucleotide sequences of the present invention makes this line of diagnosis possible. To that end, the sequence of nucleotides defining the isolated nucleic acid molecule of the present invention may provide molecular markers useful in the diagnosis of possible defects in the genome of plant material, using straightforward molecular techniques that are well established and known in the art.

In addition to use as a molecular marker, the isolated nucleic acid molecules set forth herein may facilitate the correction of any discovered genetic defect, through the complementation of the endogenous genetic sequence. To achieve this, the nucleic acid molecule defined herein may be used in the preparation of chimeric genetic constructs that can be inserted into vectors for transformation into a cell or cells of plant material, which is then regenerated into plantlets and fully grown plants. The transformed and regenerated plantlets are thereby provided with the desired trait by, for example, complementation of the relevant genetic locus.

"Chimeric genetic constructs" generally comprise, in addition, one or more regulatory regions such as inter alia promoters and 5' up-stream enhancer regions and 3' terminator sequences. These may be derived from any suitable heterologous genetic material, and are operably linked to the nucleic acid molecule of the present invention to generate the chimeric construct. By "operably linked" is meant that transcriptional and translational regulatory nucleic acids are positioned relative to a functional coding region in such a manner that the functional coding region is transcribed and optionally translated into a polypeptide. The term "functional" includes a nucleotide sequence which encodes a peptide, polypeptide or protein, or which exhibits some other function such as but not limited to binding to DNA or RNA. The transformed plant material is thereby provided with a fully functional genetic unit which is capable of being integrated into the genome and which may be expressed by the transgenic plant. Alternatively, the introduced construct may exist extra-chromosomally. In the context of the present invention, "expressed" may refer to one or more or both of the transcription and translation of the introduced nucleotide sequence by the plant.

Plants of the present invention include monocotyledonous and dicotyledonous plants, but are preferably monocotyledonous plants. Particularly preferred monocotyledonous plants are oil palm plants of the species E. guineensis and E. oleifera.

Chimeric constructs further comprise 5' sequences, including a promoter sequence for driving the expression of the operably linked nucleic acid molecule. Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e.: upstream activating sequences, enhancers and silencers) which alter gene expression in response to developmental and/or external stimuli, or in a tissue-specific manner. A promoter is usually, but not necessarily, positioned upstream or 5' of a structural gene region, the expression of which it regulates. Furthermore, the regulatory elements comprising a promoter are usually positioned within 2 kb of the start site of transcription of the gene. In the construction of heterologous promoter/structural gene combinations, it is generally preferred to position the promoter at a distance from the gene transcription start site that is approximately the same as the distance between that promoter and the gene it controls in its natural setting. As is known in the art, however, some variation in this distance can be accommodated without loss of promoter function.

The promoter may regulate the expression of the structural gene component constitutively, or differentially with respect to the cell, tissue or organ in which expression occurs or, with respect to the developmental stage at which expression occurs, or in response to external stimuli such as physiological stresses, or pathogens, or metal ions, amongst others.

Preferably, the promoter is capable of regulating expression of a nucleic acid molecule in a eukaryotic cell, tissue or organ, at least during the period of time over which the target gene is expressed therein and more preferably also immediately preceding the commencement of detectable expression of the target gene in said cell, tissue or organ.

Plant-operable and animal-operable promoters are particularly preferred for use in the construct of the present invention. Examples of preferred promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, CaMV 35S promoter, SCSV promoter, SCBV promoter and the like.

As mentioned above, the construct preferably contains additional regulatory elements for efficient transcription; for example, a 3' terminator sequence.

The term "terminator" refers to a DNA sequence at the end of a transcriptional unit, which signals termination of transcription. Terminators are 3'-non-translated DNA sequences containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants or synthesized de novo. In the context of the present invention, the terminator may be any terminator sequence that is operable in the cells, tissues or organs in which it is intended to be used.

Examples of terminators particularly suitable for use in the various nucleotide sequences of the present invention include the SV40 polyadenylation signal, the HSV TK polyadenylation signal, the CYC1 terminator, ADH terminator, SPA terminator, nopaline synthase (NOS) gene terminator of Agrobacterium tumefaciens, the terminator of the cauliflower mosaic virus (CaMV) 35S gene, the zein gene terminator from Zea mays, the Rubisco small subunit gene (SSU) gene terminator sequences, subclover stunt virus (SCSV) gene sequence terminators, any rho-independent E. coli terminator, or the lacZ alpha terminator, amongst others. Those skilled in the art will be aware of additional terminator sequences, which may be suitable for use in performing the invention. Such sequences may readily be used without any undue experimentation.

In an alternative embodiment, chimeric genetic constructs may comprise a nucleotide sequence defining a genomic region of EgMADS1, beginning from either the "ATG" start codon or the putative transcription initiation site, and including the 3' termination sequence located following the "TAA" stop codon. Either way, chimeric genetic constructs so constituted may then be cloned into suitable vectors for the transformation of target plant material, in order to deliver the means for adding or subtracting a desirable trait or phenotype.

By "vector" is meant a nucleic acid molecule, preferably a DNA molecule derived, for example, from a plasmid, bacteriophage, or plant virus, into which a genetic construct may be inserted or cloned. A vector preferably contains one or more unique restriction sites and may be capable of autonomous replication in a defined host cell, including a target cell or tissue or a progenitor cell or tissue thereof. The vector may contain any means for assuring self-replication. Alternatively, it may be integrable with the genome of the defined host such that the cloned sequence is reproducible. Accordingly, the vector may be an autonomously replicating vector, (i.e. a vector that exists as an extra-chromosomal entity, the replication of which is independent of chromosomal replication; for example, a linear or closed circular plasmid), an extra-chromosomal element, a mini-chromosome, or an artificial chromosome.

A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a second chimeric genetic construct, which comprises a selectable marker, such as an antibiotic resistance gene that can be used for selection of suitable transformants. Examples of such resistance genes are well known to those of skill in the art.

Accordingly, another aspect of the present invention is directed to a genetic construct comprising a nucleotide sequence selected from SEQ ID NO:1 or SEQ ID NO:3 to SEQ ID NO:6 inclusive or a nucleotide sequence having at least 70% identity to one or more of SEQ ID NO:1 or SEQ ID NO:3 to SEQ ID NO:6 inclusive or a nucleotide sequence capable of hybridizing to SEQ ID NO:1 or SEQ ID NO:3 to SEQ ID NO:6 inclusive or a complementary form of the sequences under low stringency conditions at 42° C.

Once constructed, genetic constructs may be cloned into a suitable vector for delivery, via any number of methods, into target plant material.

Terms such as "hybridization", "hybridizing" and the like are used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

"Stringency" as used herein, refers to the temperature and ionic strength conditions, and presence or absence of certain organic solvents, during hybridization and washing procedures. The higher the stringency, the higher will be the degree of complementarity between immobilized target nucleotide sequences and the labelled probe polynucleotide sequences that remain hybridized to the target after washing.

"Stringency conditions" refers to temperature and ionic conditions under which only nucleotide sequences having a high frequency of complementary bases will hybridize. The stringency required is nucleotide sequence dependent and depends upon the various components present during hybridization and subsequent washes, and the time allowed for these processes. Generally, in order to maximize the hybridization rate, non-stringent hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately stringent washing conditions are selected to be about 15 to 30° C. lower than the $T_m$. Highly permissive (low stringency) washing conditions may be as low as 50° C. below the $T_m$, allowing a high level of mismatching between hybridized sequences. Those skilled in the art will recognize that other physical and chemical parameters in the hybridization and wash stages can also be altered to affect the outcome of a detectable hybridization signal from a specific level of homology between target and probe sequences.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m$=69.3+0.41 (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974.). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Suitably, the isolated nucleic acid molecule has at least greater than 70% (for example, 71%), preferably at least about 75%, more preferably at least about 80%, more preferably yet at least about 85%, still more preferably at least about 90% and even still more preferably at least about 95% sequence identity to the nucleotide sequence set forth in SEQ ID NO:1 or SEQ ID NO:3.

The term "similarity" as used herein includes exact identity between compared sequences at the nucleotide or amino acid level. Where there is non-identity at the nucleotide level, "similarity" includes differences between sequences, which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window", to identify and compare local regions of sequence similarity. A "comparison window" refers to a conceptual segment of typically 12 contiguous residues that is compared to a reference sequence. The comparison window may comprise additions or deletions (that is, gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA), or by inspection and the best alignment (i.e. resulting in the highest percentage homology over the comparison window) generated by any of the various methods selected. Reference also may be made to the BLAST family of programs as for example disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e.: the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

A particularly preferred embodiment of the instant invention provides an isolated nucleic acid molecule comprising a sequence of nucleotides substantially as set forth in SEQ ID NO:1 or SEQ ID NO:3. Furthermore, although the present invention is particularly exemplified with respect to oil palm plants, this is done with the understanding that the instant invention extends to any monocotyledonous plant. Reference herein to a monocotyledonous plant includes any member of the plant family Gramineae, Palmae, Juncaceae and Achenes, but is not limited to cereals, grasses, maize, sugar cane, oats, wheat, barley as well as oil palm.

Accordingly, once a chimeric genetic construct has been cloned into a vector and transformed into target plant material, the exogenously introduced EgMADS1 coding sequence of the present invention may be translated by the cell to cause the production of the encoded protein, in this case a transcription factor. The action of the introduced protein may effect a desirable phenotype that would otherwise not be present. In this regard, particularly preferred phenotypes include the correction and/or prevention of the occurrence of an abnormal mantled phenotype.

In a related embodiment, the present invention therefore provides a vector for use in generating transgenic plants exhibiting modified phenotypes, said transgenic plants producing a polypeptide as set forth in SEQ ID NO:2 or an amino acid sequence having at least 70% similarity to SEQ ID NO:2.

Means of introducing the vectors and chimeric genetic construct(s) of the present invention into a cell, cells or tissues (i.e. transfecting or transforming target cell, cells or tissues) are various and are well known to those skilled in the art. The technique used may vary depending on the known successful techniques for that particular organism. Possible techniques include but are not limited to, transformation using $CaCl_2$ and variations thereof; direct DNA uptake into protoplasts; PEG-mediated uptake to protoplasts; electroporation; micro-injection of DNA; micro-particle bombardment of tissue explants or cells; vacuum-infiltration of tissue with nucleic acid, and T-DNA-mediated transfer from *Agrobacterium* to the plant tissue.

By way of example, for micro-particle bombardment of cells, a micro-particle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). Examples of micro-particles suitable for use in such systems include 0.1 to 10 μm and more particularly 0.5 to 5 μm tungsten or gold spheres. The DNA construct may be deposited on the micro-particle by any suitable technique, such as by precipitation.

Plant tissue capable of subsequent clonal propagation, whether by organogenesis or embryogenesis, may be transformed with a chimeric genetic construct of the present invention and a whole plant generated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g. apical meristem, axillary buds, and root meristem), and induced meristem tissue (e.g. cotyledon meristem and hypocotyl meristem).

The regenerated transformed plants may be propagated by a variety of means, such as by clonal propagation or classical breeding techniques. For example, a first generation (or T1) transformed plant may be selfed to give homozygous second generation (or T2) transformant, and the T2 plants further propagated through classical breeding techniques.

Transformed regenerated plantlets thereby generated may then exhibit a modified phenotype, by virtue of the effect of the exogenously introduced nucleotide sequence. For example, the introduction of a vector comprising a chimeric construct comprising a sequence encoding a MADS-like polypeptide, as set forth in SEQ ID NO:2, may result in the proper and normal differentiation and development of flower structure, where an abnormal mantled phenotype may otherwise have been produced.

Hence, another aspect of the invention provides an isolated polypeptide or a biologically active fragment thereof, said polypeptide comprising an amino acid sequence set forth in SEQ ID NO:2 or an amino acid sequence having at least 70% similarity to the sequence set forth in SEQ ID NO: 2.

It is to be understood that, as was the case for the isolated nucleic acid molecules set forth herein, the isolated polypeptide of the present invention also extends to encompass derivatives including, for example, fragments, variants, mutants and homologues of the said sequence. A "derivative" encompasses any single or multiple amino acid deletions, additions or substitutions as well as mutants, fragments, portions or parts of said polypeptide molecule. All such deletions, additions, substitutions, mutants, fragments, portions, or parts are encompassed by the term "derivative".

Accordingly, the nucleic acid and polypeptide molecules of the present invention may be used in both a diagnostic and a therapeutic sense, to assess potentially abnormal regenerating and/or micro-propagated plant material and, where indicated, to either eliminate tissue diagnosed as being abnormal from the population, or complement the diagnosed defect through the transformation of the defective material with a suitable vector comprising a chimeric genetic construct of the present invention. Without wishing to be limited to one theory or mode of action, the introduced EgMADS1 sequence may compensate for the defective genetic locus, and facilitate the normal further development of the plant material, via the expression of the B-type MADS transcription factor thereby encoded.

A further related aspect of the present invention contemplates the transformation of, in particular, monocotyledonous plant material such as that of *Elaeis* species, with other desirable chimeric genetic constructs in order to add to or subtract from the target plant material a particular trait or phenotype. Included in such chimeric genetic constructs are 5' regions generally referred to as promoter regions, as was already described above. Many such promoter regions, useful in the generation of chimeric constructs, vectors and, ultimately, transformed plant material, are known in the art. In the context of generating the present invention, however, the inventors isolated, cloned and characterised not only a cDNA of the nucleic acid molecule referred to herein as EgMADS1, but also an approximately 1.6 kb genomic clone comprising, inter alia, the 5' upstream promoter/enhancer region and the 5' non-translated sequence, and two introns. The 5' up-stream promoter/enhancer region thereof is defined by the sequence set forth in SEQ ID NO:4.

Hence, the present invention further contemplates promoter regions that may also include associated 5' regulatory regions, which provide a mechanism whereby the control of expression of an introduced nucleic acid molecule may be effected. It may be necessary and/or desirable to direct the expression of the exogenously introduced sequence to the appropriate tissue, for example, or to cause its expression in a developmentally regulated manner. Alternatively, constitutive expression may be desirable. The contemplated promoter region of the present invention is the natural promoter of the isolated nucleic acid molecule set forth in SEQ ID NO:3 which in vivo is operably linked to the nucleic acid molecule.

Accordingly, in a related aspect, the present invention provides an isolated polynucleotide defining a 5' regulatory region and comprising a sequence of nucleotides as set forth in SEQ ID NO:4, or a sequence having at least about 70% similarity thereto or a nucleotide sequence capable of hybridizing to SEQ ID NO:4 or its complementary form under low stringency conditions at 42° C.

Reference herein to the "5' regulatory region" includes, but is not limited to, the promoter, enhancer, 5' non-translated sequence, transcription initiation start site.

The polynucleotide promoter region of the present invention may be utilized, as described above, in the generation of a genetic construct, which comprises the said polynucleotide promoter together with the nucleic acid molecule of the present invention and appropriate 3' sequences. The 3' sequences may be those also derived from the same isolated and cloned genetic sequences set forth herein or, alternatively, may be derived from other heterologous sequences. Furthermore, the polynucleotide promoter may be utilized in the generation of a chimeric genetic construct, which comprises the said promoter together with other heterologous nucleic acid sequences. Hence, the isolated polynucleotide promoter may be used to drive the expression of any genetic sequence capable to being used to provide and/or withdraw a particular phenotype to or from a target cell into which it is introduced.

Preferably the target cell is derived from a plant of the genus *Elaeis* and, in particular, *E. guineensis* and *E. oleifera*.

Therefore, the nucleic acid sequences disclosed herein may be applied to alter or modulate a particular trait/phenotype of a target cell or tissue in a plant and preferably a plant of the species *E. guineensis* or *E. oleifera*. The particular trait may be that known as the mantled phenotype or it may be one of any number of other traits. Modulation may be effected, for example, by providing the cDNA encoding the absent or affected transcription factor, or by providing a genomic clone thereof complete with its associated intron sequences, in either case driven by its own or a heterologous promoter region. Alternatively, modulation may be effected by providing a chimeric genetic construct comprising the polynucleotide promoter of the present invention driving another heterologous nucleic acid sequence. The terms "modulating" and "modulate" include up-regulating and down-regulating expression of the subject nucleic acid molecule or levels of the instant polypeptide.

Particularly desired phenotypes contemplated herein include, for example, male sterility by producing a toxic or otherwise harmful product specifically in the stamens.

Accordingly, still another aspect of the present invention contemplates a method for generating a plant with a modified phenotype, said method comprising introducing into the genome of a plant cell or group of plant cells a genetic construct comprising a polynucleotide promoter region or functional equivalent thereof operably linked to a nucleotide sequence encoding a MADS-like polypeptide having an amino acid sequence as set forth in SEQ ID NO:2 or an amino acid sequence having at least 70% similarity to the sequence set forth in SEQ ID NO: 2.

In a preferred embodiment, the polynucleotide promoter region is that set forth in SEQ ID NO:4 or a sequence having at least about 70% similarity thereto.

In an alternative preferred embodiment, the polynucleotide promoter region may be any other suitable promoter, of which there are numerous known in the art.

In yet another alternative embodiment, the modified trait or phenotype may be effected via modulation of the expression of an endogenous gene, using an introduced genetic construct comprising, for example, selected genomic intron and/or exon sequences. This aspect of the present invention is based on the proposal that intron and exon sequences are involved in genetic networking. The introns or exons may act as receiver sequences or signal sequences.

Yet another aspect of the present invention therefore contemplates an intron defined by an isolated genomic sequence comprising a sequence of nucleotides as set forth in SEQ ID NO:5 or SEQ ID NO:6 or a sequence having at least about 70% identity thereto or a sequence capable of hybridizing to SEQ ID NO:5 or SEQ ID NO:6 or complementary forms thereof under low stringency conditions at 42° C.

The present invention extends to and encompasses plants and parts of plants, such as flowering and reproductive parts including seeds, transformed with one or more genetic constructs as set forth herein.

Preferably, the transformed plant or part of said plant is of the genus *Elaeis* and, in particular, *E. guineensis* and *E. oleifera*.

The present invention is further described by the following non-limiting Examples.

EXAMPLE 1

Cloning of the MADS1 Gene from *E. guineensis*

(a) PCR with Degenerate Primers

One strategy to obtain a B-type gene from oil palm is the use of a degenerate primer that recognizes a conserved region specific for B-type genes. Limited homology among B-type genes outside the MADS box region has been suggested by Purugganan et al. *Genetics* 140: 345-356, 1995. Based on this, B-type genes from the EMBL/Genbank databases were aligned, and regions of sufficient homology were sought. One region was found in the K-box domain of the genes. Based on this homology, a new primer was designed KBOX-DOWN [SEQ. IN NO: 10].

A PCR reaction using the KBOX-DOWN primer in combination with either primer MADS5' [SEQ. IN NO:8] or MADS5'B [SEQ. IN NO:9], i.e. primer MADS5' optimized for B-type MADS box genes) yielded a few bands on an agarose gel. The bands were cut from the gel, re-amplified and checked for presence of the MADS box region using the MADS5' and MADS3' [SEQ. IN NO:7] primers, positioned at the 5' and 3' end of the MADS box and facing to each other. Sequences of the primers used are defined in Table 2.

The band, kbox-a, gave a strong 110 bp product signal with the MADS5' and MADS3' [SEQ ID NO:7] primers. This kbox-a fragment was cloned into the pCR2.1-TOPO vector (TOPO TA cloning kit, Invitrogen). Of the 48 clones obtained, more than 50% was positive in both the MADS5'-MADS3' PCR (yielding a 110 bp fragment) and the MADS5'-KBOX-DOWN PCR (producing a 0.8 kb fragment). Six clones, with three different insert lengths, were sequenced, and compared to known MADS box gene sequences and to the EMBL nucleic acid database. While two clones gave sequences with no homology in the database, the sequence of four of the clones was identical, and highly similar to cDNA sequences of B-type MADS box genes of other plants. One of them, hereafter called "Kbox2a", was used further on. It contains a 774 bp fragment in vector pCR2. I-TOPO in *E. coli* TOP10F' (Invitrogen). This sequence is encompassed by the term "EgMADS1".

Exon-intron boundaries were determined on the basis of consensus splice sites (5'-ends of introns start with GT, 3'-ends of introns end with AG preceded by an AT-rich stretch) and similarity to the cDNA sequences of the other B-type genes.

The proposed cDNA sequence of EgMADS1 was translated in silico, and the resulting protein sequence was aligned to the translated sequences of the other B-type genes. EGMADS1 is most similar to the other two B-type genes from the monocot rice, OsMADS2 and OsMADS4 (81% similarity at protein level).

(b) Genome Walking

To obtain the remaining 5'-part of the gene and 5'-flanking sequences, including part of the promoter region, a genome walking strategy was used on genomic DNA of oil palm, digested with a number of restriction enzymes (EcoRV, DraI, HpaI, PvuII, SspI) and ligated to linkers. For the genome walking procedure, a number of primers that would allow the use of nested PCR reactions were designed. PCR reactions were done using a combination of a EgMADS1-specific primer and a primer complementary to the linker. The first linker primer matches the 5'-overhang of the long linker. This primer will only bind when the 5'-overhang is filled in. By blocking the 3'-end of the short strand, the presence of a complementary sequence, and therefore binding of the linker primer, is dependent on synthesis of a second strand primed from a EgMADS1-specific primer, thereby increasing specificity of the PCR. The 3'-end of the short linker-strand is blocked by mismatching of the last two 3'-nucleotides.

TABLE 2

2. Primers designed for amplification of MADS box genes from oil palm

| Name | Location and direction of amplification | Primer sequence |
|---|---|---|
| consensus degenerate primers[1] | | |
| | into MADS box from 3' end | 5'-ACCTC[A/G]GC[A/G]TC[A/G]CA[A/G] AG[G/C]AC-3' [SEQ ID NO: 7] |
| MADS5' | into MADS box from 5' beginning | 5'-AG[C/T]T[C/G]AAG[C/A]GGAT[A/C]G AGAAC-3' [SEQ ID NO: 8] |
| MADS5'B | into MADS box, optimized for B-type genes | 5'-AAGAT[C/A]AA[G/A]AG[G/A]AT[C/A] GAGAAC-3' [SEQ ID NO: 9] |
| KBOX-DOWN | from K-box towards MADS-box, optimized for B-type genes | 5'-AT[A/G]TT[A/G]TC[A/G]TT[G/C]T CT TTCTTG-3' [SEQ ID NO: 10] |
| MADS17 | from end of coding sequence towards K-box, based on rice B-type genes | 5'-ACCC[G/T]GAAGGTGA[T/A]CGGC ATC-3' [SEQ ID NO: 11] |
| | in middle of MADS box, based on oil palm MADS boxes | 5'-CG[C/G]CG[C/T]TTI[C/G][C/A][G/A]AAIGTIACCTG[G/C]C-3' [SEQ ID NO: 12] |
| b. Primers designed on the EgMADS1 (clone Kbox2a) sequence | | |
| | towards K-box | 5'-CAAGATGTCCGAGTACTGCAG-3' [SEQ ID NO: 13] |
| MADS11 | towards MADS box | 5'-CTGCAGTACTCGGACATCTTG-3' [SEQ ID NO: 14] |
| MADS12 | towards K-box | 5'-GCTGTCGAGGATTCTCGAGAG-3' [SEQ ID NO: 15] |
| MADS13 | towards MADS box | 5'-CTCTCGAGAATCCTCGACAGC-3' [SEQ ID NO: 16] |
| MADS14 | towards K-box | 5'-GAGGTACCAGCATAACTCTGG-3' [SEQ ID NO: 17] |
| MADS15 | towards MADS box | 5'-CCAGAGTTATGCTGGTACCTC-3' [SEQ ID NO: 18] |

TABLE 2-continued

2. Primers designed for amplification of MADS box genes from oil palm

| Name | Location and direction of amplification | Primer sequence |
|---|---|---|
| | Pimers designed on the Hpa 1.6 kb genomic fragment | |
| | towards coding sequence | 5'-GAGAAGATACTCAATTCTTGCAC-3' [SEQ ID NO: 19] |
| MADS19 | towards promotor | 5'-TGTGTACTCGTACTAATCGAG-3' [SEQ ID NO: 20] |
| MADS20 | towards coding sequence | 5'-AGGTGAGTAAAATGTCATAGC-3' [SEQ ID NO: 21] |
| Linker sequences and primers complementary to the linkers | | |
| Linker-long[2] | 5'-ACTCGATTCTCAACCCGAAAGTATAGATCCCA-3' [SEQ ID NO: 22] | |
| Linker-short[2] | 5'-TGGGATCTATACTTTCAA-3' [SEQ ID NO: 23] | |
| Linker short-NH2 | 5'-TGGGATCTATACTT-NH2-3' [SEQ ID NO: 24] | |
| ADAPT-Pr | 5'-ACTCGATTCTCAACCCGAAAG-3' [SEQ ID NO: 25] | |
| ADAPT-Pr2 | 5'-CAACCCGAAAGTATAGATCCCA-3' [SEQ ID NO: 26] | |
| MADS21 | 5'-AGTACACAACCCTCCATTTCCAGT-3' | |
| MADS22 | 5'-ACCAGGCATCTATTAGCACATCAA-3' | |

[1]Consensus sequences are based on a large number of MADS box genes from plants, and notably on the sequences available from monocotyledonous plants.
[2]According to Fischer et al., Proc Natl Acad Sci USA 92: 5331-5335, 1995

Successive PCRs towards the 5'-end of EgMADS1 gave the best results, starting from primer MADS15 at 60° C., followed by primer MADS11 at 60° C. In the HpaI digest, this produced a clear band of 1.6 kb. PCR with primer MADS12 followed by MADS14 on this band yielded a fragment 100 bp shorter than with primer MADS10, as predicted by the EgMADS1 sequence. Furthermore, a MADS5'-MADS3' PCR on the purified 1.6 kb fragment yielded the 110 bp fragment, and a MADS5'-MADS11 PCR a 150 bp fragment, as predicted. Therefore, the 1.6 kb fragment (designated "Hpa1.6") was cloned into vector pCR2.1-TOPO (Invitrogen) and sequenced.

Comparison with genes in the database and the previously obtained genomic EgMADS1 sequence confirmed that this fragment indeed contained the remaining 5'-part of the first exon, and ca. 1.2 kb of upstream sequence of the oil palm EgMADS1 gene.

This Hpa1.6 fragment is the result of several successive PCRs, which may result in single nucleotide mutations due to the inaccuracy of the Taq polymerase. Therefore, primer MADS18 (at the 5'-end of the Hpa1.6 fragment) and primer MADS11 were used in a single PCR on oil palm genomic DNA with a proof-reading Taq polymerase, to obtain a reliable 5'-flanking sequence of the EgMADS1 gene.

5'-RACE (Rapid Amplification of cDNA Ends) experiments were performed with oil palm RNA to locate the transcription start site of the EgMADS1 gene. The 5'/3'-RACE kit of Boehringer Mannheim on total RNA from an oil palm female inflorescence (6 cm long) was used. Total RNA (1 µg) was used as a template in first strand cDNA synthesis from primer MADS15, using reverse transcriptase. The resulting single stranded DNA was polyA-tailed with terminal transferase. Then, PCR was performed with a second (nested) EgMADS1-specific primer (MADS13) and a polyT primer with an adaptor-tail (a component of the kit). A second PCR with a third gene-specific primer and the adaptor primer resulted in a single fragment of ca 500 bp, which was subcloned into pCR2.1TOPO. Nine positive clones were end-sequenced. One contained no insert. The location of the 5'-ends of the eight remaining clones was determined.

(c) Isolation of the 3' Coding Region

Using total RNA of female and male oil palm inflorescences, RT-PCR was performed to obtain the remainder of the 3' coding sequence. The first step in this strategy involved the synthesis of first strand cDNA from a total RNA sample, using Reverse Transcriptase (Clontech) and a poly(dT) primer. This primer binds to the Poly(A) tail present in almost all mRNAs. The second strand cDNA was then amplified using only the first specific EgMADS1 primer MADS10 for 30 cycles (linear amplification). This was followed by a PCR with MADS10 and a mixture of poly(dT) anchor primers. At the 3'-end of these primers there are two additional (non-T) nucleotides. These direct the primer towards the 5'-end of the poly(A) tail. The 5'-end of the primer consists of a sequence of 15 nucleotides, allowing increased annealing temperatures after the first few cycles in the PCR, thereby increasing the specificity of the amplification. The product of this last PCR is used as a template in a PCR with a second (nested) EgMADS1-specific primer, MADS12, and the poly(dT) primer mixture.

The product was analyzed on an agarose gel, and contained two major bands of approximately 700 bp and 850 bp. These bands were cloned into the pCR-TOPO vector (Invitrogen) and a number of clones was analyzed by sequencing and BLAST similarity searches with the Genbank databases. Several of the 700 bp clones were found to contain most of the remaining cDNA sequence of the EgMADS1 gene. The sequence includes the 3'-part of the coding region, as well as the 3'-non-coding region until the poly(A) tail. The cDNA sequence confirms the previously proposed locations of intron-exon boundaries for intron 2 and exons 2 and 3.

(d) Amplification of EgMADS1 Full Length Coding Sequence

To obtain a reliable coding sequence the entire coding sequence was isolated in a single clone by RT-PCR with primers situated in the 5' (upstream, MADS21) and the 3' (downstream, MADS22) non-coding regions of the EgMADS gene. Total RNA was isolated from oil palm male inflorescences (23 cm in length). First strand cDNAs (synthesised with the cDNA for PCR kit, Clontech) of RNA samples from several tissues were used as a template for a PCR reaction with the primers MADS21 and MADS22, yielding a single PCR product. This product was excised from an agarose gel, and subcloned into the PCR21.TOPO vector. The insert sequences of several clones were determined, and shown to contain the full length coding sequence of EgMADS1.

The combination of the sequence of the genomic Hpa 1.6 kb fragment and the 700 bp cDNA clones described above results in the full length cDNA sequence and approximately 1.2 kb of upstream sequence of the oil palm EgMADS1 gene.

The nucleotide sequence of the protein encoding DNA (CDS) is referred to herein as SEQ ID NO:1.

The cDNA sequence from the putative transcription initiation site, including the 5' non-translated region, the CDS, and the 3' non-translated region, is set forth in FIG. 1 and is referred to herein as SEQ ID NO:3. The predicted amino acid sequence, as translated in silico, is referred to herein as SEQ ID NO:2.

The entire sequence, whether derived from genomic DNA or from cDNA/mRNA is set forth in FIG. 2 and comprises the nucleotide sequence defining the cDNA as well as the introns and the 5' non-translated sequence, promoter regions (ie. 5' regulatory region) and the 3' regulatory region.

The full genomic sequence includes the EgMADS1 promoter region including the 5' non-translated sequence, which extends from position 1 to position 1447 of the sequence in FIG. 2. The nucleotide sequence defining the EgMADS1 5' regulatory region is referred to herein as SEQ ID NO:4.

EXAMPLE 2

Expression Analysis of EgMADS Genes

Expression analysis of EgMADS genes was assayed in two ways: by Northern blotting and by gene-specific RT-PCR.

(a) Northern Blotting

Oil Palm inflorescence RNA from different stages of development was electrophoresed on MOPS-formaldehyde agarose gels, according to standard procedures. Three identical blots were made. The RNA was transferred to Hybond N filters by capillary blotting in 20×SSC, and hybridized to $^{32}$P-radioactively labeled cDNA fragments of the EgMADS genes. The probes (containing the 3'-parts of the EgMADS genes) were isolated by PCR and excision from agarose gels. Blots were hybridized in standard dextrane sulphate-containing hybridization solution at 65° C., and washed to a stringency of 0.1% v/v SSC, 0.5% w/v SDS at 65° C. Blots were exposed to phosphoimager plates and X-ray films.

None of the blots showed a specific signal with any of the cDNA probes. Several new attempts also failed to produce acceptable Northern blots.

(b) Gene-Specific RT-PCR

Messenger RNA expression of the EgMADS genes was also analyzed by Reverse Transcriptase (RT)-PCR. RT-PCR is more sensitive than Northern blotting, but it is not quantitative, so small differences in expression levels are not detected. However, presence/absence differences can be reliably detected.

For this, two primers for each of the EGMADS genes were designed, for gene-specific amplification in RT-PCR. First strand cDNAs (synthesised with the cDNA for PCR kit (Clontech) of RNA samples from several tissues were used as a template. Tissues sampled included vegetative shoots, 1 cm-13 cm male and female inflorescences of normal oil palms, and 1 cm-13 cm male and female inflorescences of abnormal (mantled phenotype) oil palms.

The PCR products were visualized on ethidium bromide-stained agarose gels (refer to FIG. 3). EgMADS1 was detected in all tissues examined.

EXAMPLE 3

Sequence Analysis of EgMADS1 in Genetically Mantled Oil Palm

EgMADS1 is a B-type MADS box gene, and is likely to be involved in specifying petals and stamens. Although no expression differences were found when comparing tissue from normal and mantled plants, it is still possible that EgMADS1 is affected somehow in the mantled plants.

Mutant oil palm plants that display the mantled phenotype are available. Therefore, the EgMADS1 sequences in both normal and genetically mantled oil palm have been examined, to see whether this gene is impaired/disrupted in the mutant, which would be a strong indication of involvement of EgMADS1 in establishing the mantled phenotype.

For this, the already-available PCR primers were used to amplify parts of the EgMADS1 gene in genomic DNA from both normal (2 samples, Eg1A and Eg2A) and mutant oil palms (4 samples). Three primer combinations were used for amplifying EgMADS1 fragments: MADS18 and MADS19 amplified a 1,200 bp fragment of the promoter region, MADS21 and MADS15 amplified a 600 nt fragment of the 5'-region of the gene, and MADS12 and MADS1R were used to amplify a region more to the 3'-part of the gene. The fragment generated by the latter combination was over 2 kb in size: to be able to produce an overlapping sequence from both strands, the "k-Box down" primer was used instead of the MADS1R primer. This generated a 600 bp fragment. The PCR products of the three primer combinations from both mantled and normal DNA were used for direct sequencing, and the sequences were compared.

The 18/19 combination and the 21-15 combination fragments were aligned with previously obtained sequences from the EgMADS1 gene. A single mutation (at position "−1274", G becomes A) was detected in the sequence from the genetically mantled plants. The sequence surrounding the mutation does not indicate that this is part of a regulatory sequence; neither does the location, which is more than 1,200 nt upstream of the transcription start site.

EXAMPLE 4

Transgenic Analysis of EGMADS1 Function

Figure 5:
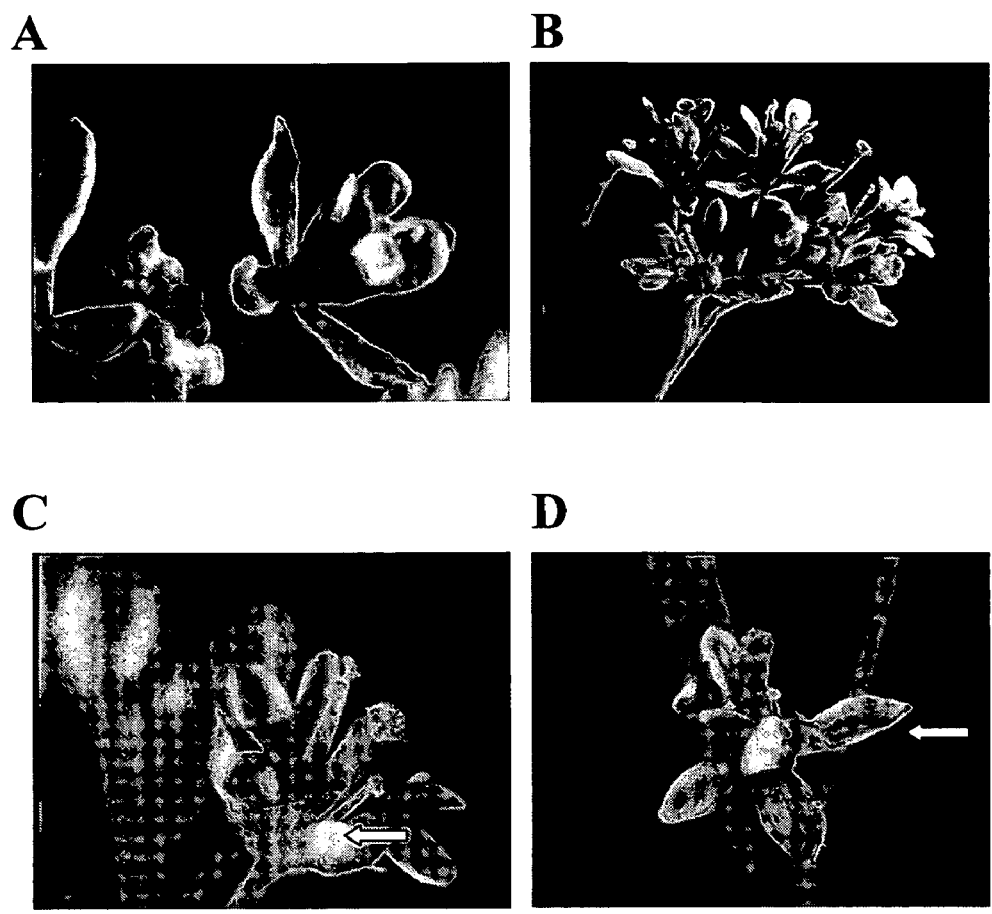
FIG. 5 is a photographic representation of flowers of transgenic *Arabidopsis* plants, transformed with a construct comprising the EGMADS1 gene of the present invention. Flowers of some of the over-expressor lines show a partial conversion of sepals into petals in the first whorl, indicated by arrows (C and D).
Figure 6:
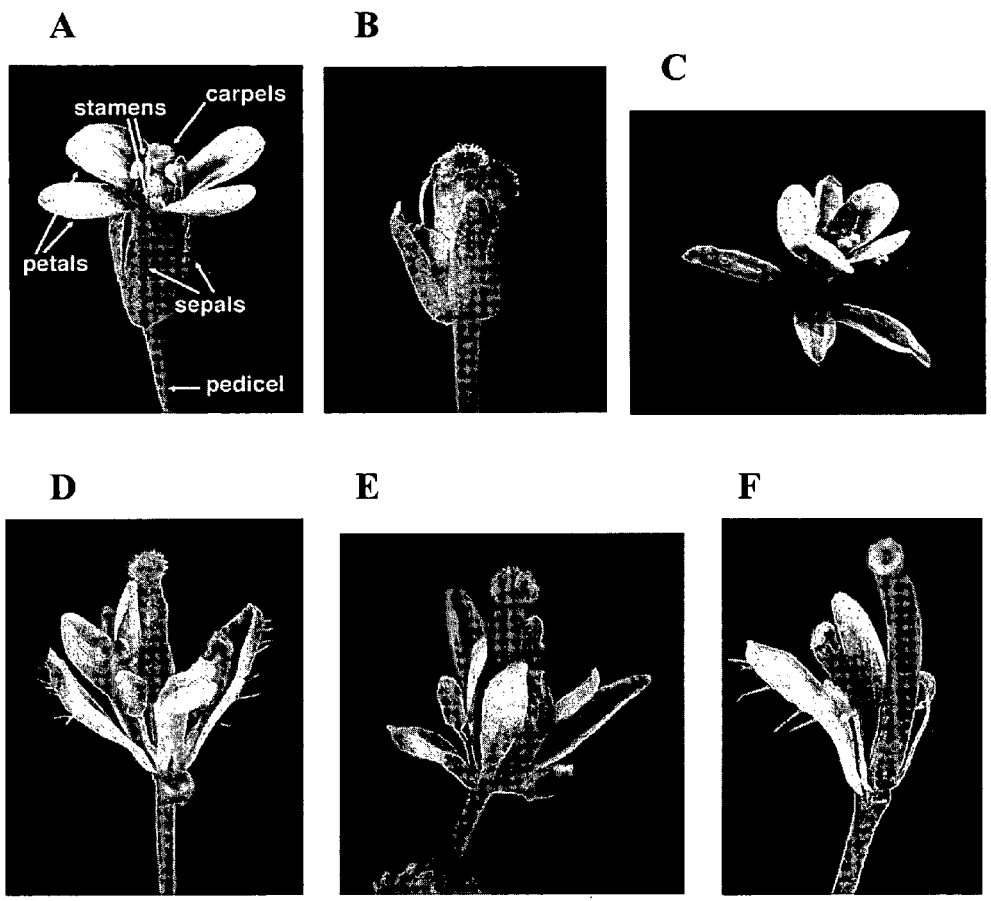
FIG. 6 is a photographic representation of flowers of a wild type *Arabidopsis* plant (A), pi mutant (B), a transgenic over-expressor line, comprising the EgMADS1 sequence (C), and transgenic F2 lines that show partial complementation of the pi phenotype (D-F), effected by the introduced EgMADS1 sequence. The partially complemented flowers have petalloid whorl 1 organs derived from the over-expression phenotype, restored petals in whorl 2, stamen/carpel structures in whorl 3 and an unaffected pistil in whorl 4.

A full-length clone of EgMADS1 was generated (see example 1d), subcloned into a transformation construct and transformed into a B-type *Arabidopsis thaliana* mutant to see whether this oil palm B-type gene was able to complement the mutation, and to a wild type *A. thaliana*, to analyze the phenotypic effects of over-expression of EGMADS1 in *Arabidopsis*. The results, which may be seen in FIGS. 5 and 6, provided clear evidence for a B-type function for EgMADS1.

EgMADS1 is most likely the oil palm ortholog of the *Arabidopsis* B-type MADS-box gene PISTILLATA (PI). This *Arabidopsis* gene is responsible for the determination of petal and stamen identity and suppression of its function leads to the formation of sepals and carpels in the second and third whorl, respectively. PI is active in a combinatorial manner together with APETALA3 (AP3), representing the B function (Samach et al., *Plant Cell* 9: 559-570, 1997). Over-expression of both genes resulted in a transformation of sepals into petals and carpels into stamenoid tissue, all in accordance to the ABC model (Coen and Meyerowitz, *Nature* 353: 31-37, 1991) for floral organ identity.

For the functional characterization of the oil palm gene, EGMADS1, the following two strategies were used:

(a) 35S::EgMADS1 Over-Expression in Wild Type *Arabidopsis* (Ecotype Col).

Although both AP3 and PI are needed to activate the B function, partial transformation of sepals into petals were expected, because AP3 is "leaky" in the first whorl.

(b) Complementation of the *Arabidopsis* Pi Mutant with 35S::EgMADS1.

The *Arabidopsis* PI gene and other homologs can partly complement the *Arabidopsis* pi mutant. Similarly, the oil palm ortholog of PI may be able to complement this phenotype, at least partly, as was shown by other heterologous PI-like genes (Lamb and Irish, PNAS 100: 6558-6563, 2003)

Strategy (a)

Wild type *Arabidopsis* plants (Col) were transformed with a binary construct containing full length EGMADS1 (see example 1d), driven by the 35S promoter. Transformants (48) were obtained, from which approximately 30% showed an aberrant phenotype. Aberrations were observed in the first whorl, which showed chimeric organs of petalloid-sepalloid identity (refer to FIG. 4). Also, the positions of these first whorl organs were changed, when compared to wild type sepals. This demonstrates that the EGMADS1 gene is functional to determine petal identity. Whether it is also able to specify stamen identity can not be concluded from this experiment. However, since the B function is responsible for both petals and stamens, these results indicate that EgMADS1 is the oil palm ortholog of PI.

Strategy (b)

For the complementation of the *Arabidopsis* pi mutant, this mutant was crossed with over-expressor lines. Two lines, showing the over-expressor phenotype (see FIG. 5), were selected. F1 progeny plants, from this cross, segregated for the over-expression phenotype and all plants were hemizygous for the pi allele. In the F2 of these crosses, a (partial) complementation of the pi phenotype, demonstrating that EGMADS1 in the true ortholog of PI, was expected.

In the F2 of these crosses, a (partial) complementation of the pi phenotype is expected, which would demonstrate that EGMADS1 is the true ortholog of PI. For both crosses, 54 plants were analyzed in the F2. FIG. 6 shows the results of the complementation of the pi mutant. FIGS. 6D-F show the floral phenotype obtained by the partial complementation of the pi mutant by EGMADS1 over-expression. The over-expression phenotype of EgMADS1 is still visible in the first whorl, which causes a change of sepals into petalloid structures. Changes in the second and third whorl show the partial complementation of the pi phenotype. In the second whorl, sepals are converted into petals and in the third whorl a conversion of carpelloid structures into stamenoid structures is visible. In other flowers the conversion into stamens is even stronger, resulting in the production of pollen and seed.

Plants in the F2 family (54 plants) segregated according to a Mendelian segregation. Table 3 shows the expected segregation numbers and the real numbers for two independent lines.

TABLE 3

Segregation numbers for F2 family

| Segregation | Wild type | pi mutant | Over-expression | Complementation |
|---|---|---|---|---|
| Expected | $3/16 = \sim 10$ | $1/16 = \sim 3$ | $9/16 = \sim 30$ | $3/16 = \sim 10$ |
| line #35[1] | 7 | 2 | 33 | 8 |
| line #49[1] | 19 | 4 | 22 | 5 |

[1]for both lines four plants are still not flowering

These results demonstrate that EGMADS1 is able to complement the pi mutant; i.e. it specifies the identity of petals and stamens. Therefore, it can be concluded that EgMADS1 represents a class B function gene with a function that is identical to the *Arabidopsis* homeotic gene PISTILLATA (PI).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

---

What is claimed is:

1. An isolated nucleic acid molecule comprising a sequence of nucleotides encoding or complementary to a sequence encoding a B-type MADS box-type transcription factor or a homolog thereof, wherein said nucleic acid molecule comprises the nucleic acid sequence as set forth in SEQ ID NO: 1 or a nucleic acid sequence having about 95% or more sequence identity to SEQ ID NO: 1 after optimal alignment wherein when said nucleic acid molecule is transformed into a B-type mutant of *Arabidopsis*, the nucleic acid molecule complements the mutant phenotype.

2. The isolated nucleic acid molecule of claim 1 wherein the nucleotide sequence encodes the amino acid sequence set forth in SEQ ID NO: 2.

3. The isolated nucleic acid molecule of claim 1 comprising the nucleotide sequence set forth in SEQ ID NO: 1.

4. The isolated nucleic acid molecule of claim 1 further comprising a 5' untranslated region and having the nucleotide sequence set forth in SEQ ID NO: 4.

5. The isolated nucleic acid molecule of claim 1 further comprising a 3' untranslated region and having the nucleotide sequence set forth in SEQ ID NO: 3.

6. The isolated nucleic acid molecule of claim 1 comprising an intron selected from the group consisting of: SEQ ID NO: 5, SEQ ID NO: 6 a nucleotide sequence capable of hybridizing under low stringency conditions to SEQ ID NO: 5 and a nucleotide sequence capable of hybridizing under low stringency conditions to SEQ ID NO: 6.

7. The isolated nucleic acid molecule of claim 1 wherein said nucleic acid is isolated from a plant is of the genus *Elaeis*.

8. The isolated nucleic acid molecule of claim 7 wherein said plant is of the species *Elaeis guineensis* or *Elaeis oleifera*.

9. A vector comprising the nucleic acid molecule of claim 1.

10. The vector of claim 9 wherein the vector is a cloning vector.

11. The vector of claim 9 wherein the vector is an expression vector.

12. The vector according to claim 9 wherein the vector is operable in a prokaryotic cell.

13. The vector according to claim 9 wherein the vector is operable in a eukaryotic cell.

14. The vector of claim 12 wherein the prokaryotic cell is a bacterial cell.

15. The vector of claim 14 wherein the bacterial cell is an *E. coli* cell.

16. The vector of claim 13 wherein the eukaryotic cell is a fungal cell.

17. The vector of claim 13 wherein the eukaryotic cell is a plant cell.

18. An isolated genetically modified cell comprising the nucleic acid of claim 1.

19. The genetically modified cell of claim 18 wherein the cell is a prokaryotic cell.

20. The genetically modified cell of claim 19 wherein the prokaryotic cell is an *E. coli* cell.

21. The genetically modified cell of claim 18 wherein the cell is a eukaryotic cell.

22. The genetically modified eukaryotic cell of claim 21 wherein the cell is a fungal cell.

23. The genetically modified eukaryotic cell of claim 21 wherein the cell is a plant cell.

24. The genetically modified plant cell of claim 23 wherein the plant cell is an *Elaeis* sp. cell.

25. The genetically modified plant cell of claim 23 wherein the plant cell is an *Arabidopsis* sp, cell.

26. A plant tissue culture comprising one or more plant cells according to claim 23.

27. A method of making a modified oil palm plant, comprising expressing the polynucleotide according to claim 1 in the oil palm plant to be modified.

* * * * *

UNITED STATES PATENT AND TRADEMARK OFFICE
CERTIFICATE OF CORRECTION

PATENT NO. : 7,863,501 B2  
APPLICATION NO. : 11/243296  
DATED : January 4, 2011  
INVENTOR(S) : Van der Linden et al.

Page 1 of 1

It is certified that error appears in the above-identified patent and that said Letters Patent is hereby corrected as shown below:

At column 42, line 6, in Claim 25, please change "sp, cell." to --sp. cell.--.

Signed and Sealed this
Twelfth Day of February, 2013

Teresa Stanek Rea
*Acting Director of the United States Patent and Trademark Office*